(12) United States Patent
Bonde

(10) Patent No.: US 12,004,940 B2
(45) Date of Patent: Jun. 11, 2024

(54) TRANSCATHETER DEVICE, SYSTEM AND METHOD FOR TREATING TYPE A AORTIC DISSECTION

(71) Applicant: YALE UNIVERSITY, New Haven, CT (US)

(72) Inventor: Pramod Bonde, Woodbridge, CT (US)

(73) Assignee: YALE UNIVERSITY

( * ) Notice: Subject to any disclaimer, the term of this patent is extended or adjusted under 35 U.S.C. 154(b) by 545 days.

(21) Appl. No.: 17/061,347

(22) Filed: Oct. 1, 2020

(65) Prior Publication Data
US 2021/0093441 A1 Apr. 1, 2021

Related U.S. Application Data

(60) Provisional application No. 62/909,144, filed on Oct. 1, 2019.

(51) Int. Cl.
*A61F 2/07* (2013.01)
*A61F 2/962* (2013.01)

(52) U.S. Cl.
CPC ............. *A61F 2/07* (2013.01); *A61F 2/962* (2013.01); *A61F 2210/009* (2013.01)

(58) Field of Classification Search
CPC ............. A61F 2/07; A61F 2210/009; A61F 2220/0008; A61F 2/88; A61F 2002/077; A61F 2/24; A61F 2/954; A61B 2017/00243; A61B 2017/00876
See application file for complete search history.

(56) References Cited

U.S. PATENT DOCUMENTS

2015/0290000 A1* 10/2015 Hansen ............... A61F 2/07
606/198

FOREIGN PATENT DOCUMENTS

| DE | 10320517 A1 * | 11/2004 | ............. A61F 2/07 |
| EP | 2957258 A1 * | 12/2015 | ............. A61F 2/04 |
| WO | WO-03099166 A1 * | 12/2003 | ............. A61F 2/88 |

OTHER PUBLICATIONS

Scheule, Endovascular prosthesis for implantation in a vessel . . . translation of DE 10320517 A1 (Year: 2004).*

* cited by examiner

*Primary Examiner* — Brian E Pellegrino
(74) *Attorney, Agent, or Firm* — Riverside Law LLP

(57) ABSTRACT

A system for treating aortic dissection includes a sinotubular junction magnetic array having a first plurality of magnetic elements, a counter-magnetic array having a second plurality of magnetic elements, and an ascending aortic stent graft comprising a third plurality of magnetic elements. A method for treating aortic dissection includes the steps of positioning a sinotubular junction magnetic array at the sinotubular junction, advancing counter magnetic constructs from the femoral vein and positioning them in the right atrium, expanding the sinotubular junction ring at a target position, advancing the counter magnetic array to form an at least partial circumferential seal, and advancing and positioning an ascending magnetic graft within an interior of the sinotubular junction magnetic array. A system for treating aortic dissection, a fixation device for anchoring an ascending aortic stent graft, and a transcatheter device for treating aortic dissection are also described.

7 Claims, 28 Drawing Sheets

422

To fit magnets into tubing for pulsatile water test, thickness needs to be less than 2 mm.

Pulsatile flow test

Pulsatile flow test

Pulsatile console contrl

| | | Flow Min | | Flow Max | |
|---|---|---|---|---|---|
| Vacuum pressure Min | 35 mmHg | 2 lpm | Low | 2.4 lpm | |
| Vacuum pressure Max | 100 mmHg | 2 lpm | | 3 lpm | High |

Pulsatile flow test 8 magnet test at High conditions

Pulsatile flow test 8 magnet test at Low and High conditions

Magnet test

TRANSCATHETER DEVICE, SYSTEM AND METHOD FOR TREATING TYPE A AORTIC DISSECTION

CROSS-REFERENCE TO RELATED APPLICATIONS

This application claims priority to U.S. provisional application No. 62/909,144 filed on Oct. 1, 2019 incorporated herein by reference in its entirety.

BACKGROUND OF THE INVENTION

Open surgical treatment is currently the only option for acute type A dissection. However, this remains highly invasive with high morbidity/mortality rates primarily due to CPB and malperfusion related phenomenon. Challenges in designing a stent are primarily due to issues related to proximal and distal graft fixation and sealing due to migratory forces.

The pathology of aortic dissection is generally as follows: Two layers of the aorta separate after a tear develops which propagates down the length of the aorta which can cut off blood coming from the branches and supplying to vital organs. When this happens in the ascending aorta, the tear can lead to severe leakage from the aortic valve and lead to acute heart failure. This can compromise blood supply to the heart and cause a massive heart attack. Resulting conditions may include patients death due to rupture, malperfusion, carotid-stroke, coronary-heart attack, aortic valve-heart failure, gut arteries (intestinal death), or renal-kidney failure.

Treatment generally involves preventing leak from the valve and preventing a heart attack by interrupting a piece of aorta and replacing it with synthetic graft material. However, this requires stopping circulation in the body and is done via an open heart procedure that takes 12 hours or more. For every one hour of delay the patient's chances of dying increase, and by the end of 24 hours 50% are dead without surgery and the rest die within a week if not treated. Dissection of the ascending aorta carries a 100% mortality if not operated on immediately. Only certain patients are considered operative candidates. Operative mortality is at 30%, and involves a complex operation that puts the patient in suspended animation (cooled to 18 degrees and then stop the heart and rely on a lung machine to allow a quick repair of the aorta). Post operative deaths are mainly due to malperfusion, a diagnosis of which can be delayed after a prolonged and complicated procedure. Given the morbid nature of the operation, many patients are not even eligible candidates. Another major cause of morbidity is organ dysfunction which can result from the prolonged bypass time and stopping of blood circulation during the procedure (hypothermic arrest).

Thus, what is needed in the art is a system, device and method to percutaneously treat type A dissection which would represent a significant advancement in the art.

SUMMARY OF THE INVENTION

In one embodiment, a system for treating aortic dissection includes a sinotubular junction magnetic array having a first plurality of magnetic elements, a counter-magnetic array having a second plurality of magnetic elements, and an ascending aortic stent graft comprising a third plurality of magnetic elements. In one embodiment, the poles of the first plurality of magnetic elements are configured to correspond with the poles of the second plurality of magnetic elements. In one embodiment, the sinotubular junction magnetic array are configured into the shape of a ring. In one embodiment, the ring is a multi-component ring. In one embodiment, the counter-magnetic array is configured into the shape of a ring. In one embodiment, the ring is a multi-component ring. In one embodiment, the ascending aortic stent graft comprises a first and second extension wing.

In one embodiment, a method for treating aortic dissection includes the steps of positioning a sinotubular junction magnetic array at the sinotubular junction, advancing counter magnetic constructs from the femoral vein and positioning them in the right atrium, expanding the sinotubular junction ring at a target position, advancing the counter magnetic array to form an at least partial circumferential seal, and advancing and positioning an ascending magnetic graft within an interior of the sinotubular junction magnetic array.

In one embodiment, a system for treating aortic dissection includes a sinotubular junction magnetic fixation array; and an ascending aortic stent graft including magnetic elements corresponding to the magnetic fixation array.

In one embodiment, a fixation device for anchoring an ascending aortic stent graft includes a sinotubular junction magnetic array having a first plurality of magnetic elements, a counter-magnetic array having a second plurality of magnetic elements and configured to form at least a partial circumferential seal with the first plurality of magnetic elements.

In one embodiment, an ascending aortic stent graft includes a plurality of magnetic fixation elements.

In one embodiment, a transcatheter device for treating aortic dissection includes an elongate flexible body having a proximal end, a distal end and an lumen extending therebetween, and a plurality of magnets disposed along an external surface of the flexible body and configured to align in a stacked configuration with the flexible body forms a helical geometry.

BRIEF DESCRIPTION OF THE DRAWINGS

The foregoing purposes and features, as well as other purposes and features, will become apparent with reference to the description and accompanying figures below, which are included to provide an understanding of the invention and constitute a part of the specification, in which like numerals represent like elements, and in which.

DETAILED DESCRIPTION OF THE INVENTION

Figure 1A:
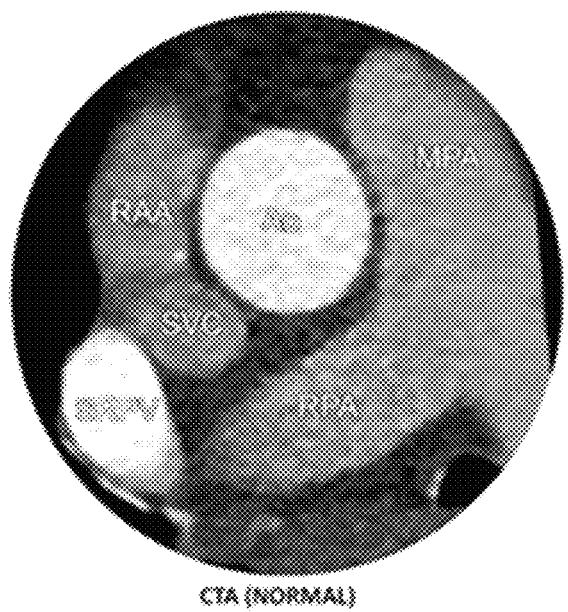
FIGS. 1A and 1B are images of a normal CTA scan (FIG. 1A) and a CTA scan showing a Type A dissection (FIG. 1B) for illustrative purposes.

It is to be understood that the figures and descriptions of the present invention have been simplified to illustrate elements that are relevant for a more clear comprehension of the present invention, while eliminating, for the purpose of clarity, many other elements found in systems and methods for treating Type A aortic dissection. Those of ordinary skill in the art may recognize that other elements and/or steps are desirable and/or required in implementing the present invention. However, because such elements and steps are well known in the art, and because they do not facilitate a better understanding of the present invention, a discussion of such elements and steps is not provided herein. The disclosure herein is directed to all such variations and modifications to such elements and methods known to those skilled in the art.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are described.

As used herein, each of the following terms has the meaning associated with it in this section.

The articles "a" and "an" are used herein to refer to one or to more than one (i.e., to at least one) of the grammatical object of the article. By way of example, "an element" means one element or more than one element.

"About" as used herein when referring to a measurable value such as an amount, a temporal duration, and the like, is meant to encompass variations of ±20%, ±10%, ±5%, ±1%, and ±0.1% from the specified value, as such variations are appropriate.

Ranges: throughout this disclosure, various aspects of the invention can be presented in a range format. It should be understood that the description in range format is merely for convenience and brevity and should not be construed as an inflexible limitation on the scope of the invention. Where appropriate, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 2.7, 3, 4, 5, 5.3, and 6. This applies regardless of the breadth of the range.

Referring now in detail to the drawings, in which like reference numerals indicate like parts or elements throughout the several views, in various embodiments, presented herein is a system and method for treating aortic dissection.

In one embodiment, a bioinspired system is based on a Monk's head mushroom geometry of the ascending aortic stent graft with magnetic external fixation. The proximal part of the stent is fixed by magnetic arrays placed within the right atrial appendage, main pulmonary artery extending to right pulmonary artery and neodymium magnets incorporated within the stent creating apposition externally to the graft and achieving over 90% circumferential seal (proximally) and within the innominate vein (distally). The distal part of the stent was designed with two flared components each extending into the innominate (e.g. 90 degrees angulation) and descending aorta (e.g. 50 degrees angulation) for preventing migration with fibrillary Dacron externally to promote adhesion and sealing. Accordingly, embodiments of a bio-inspired system exploiting critical anatomical observation with fixation within the venous system offers a less invasive option for critically unstable and sick patients with Type A dissection. Advantageously, the layers of dissected aorta can be approximated by magnetic fixation from external related vascular structures, the method prevents malperfusion and allows monitoring, no open heart surgery is needed, and the procedure can be performed in approximately 30 minutes.

Figure 1B:
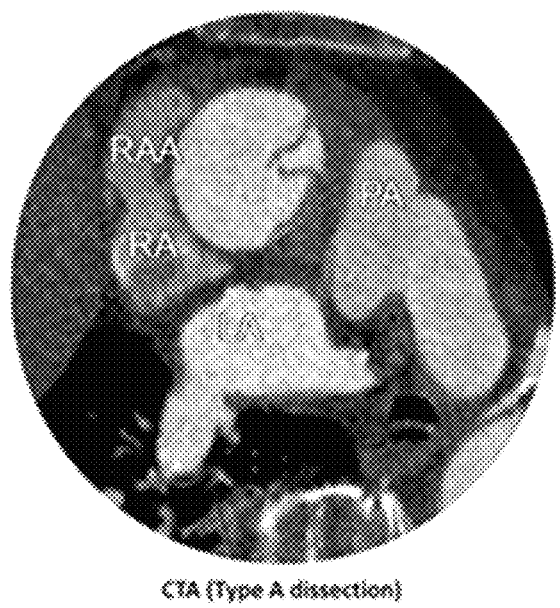

With reference now to FIGS. 1A and 1B, a normal computed tomography angiography (CTA) scan (FIG. 1A) and a CTA scan showing a Type A dissection (FIG. 1B) for illustrative purposes. A Type A dissection happens when a tear occurs in the ascending part of the aorta just as it branches off the heart. The anatomy shown in the images includes the right atrial appendage (RAA), right atrium (RA), left atrium (LA), superior vena cava (SVC), aorta (AO), pulmonary artery (PA), main pulmonary artery (MPA), right pulmonary artery (RPA) and superior right pulmonary vein (SRPV).

Figure 1C:
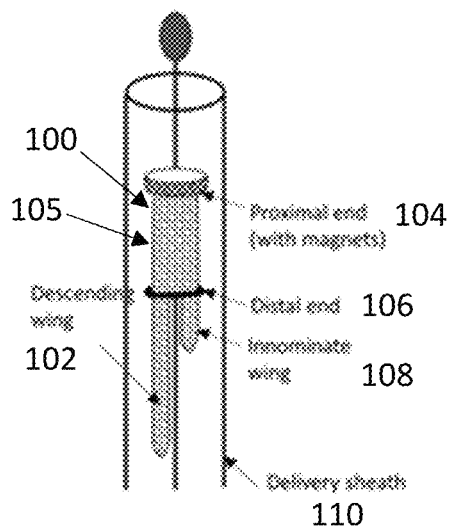
FIGS. 1C-1G show functional views of a device and system for treating aortic dissection, according to one embodiment.
Figure 1D:
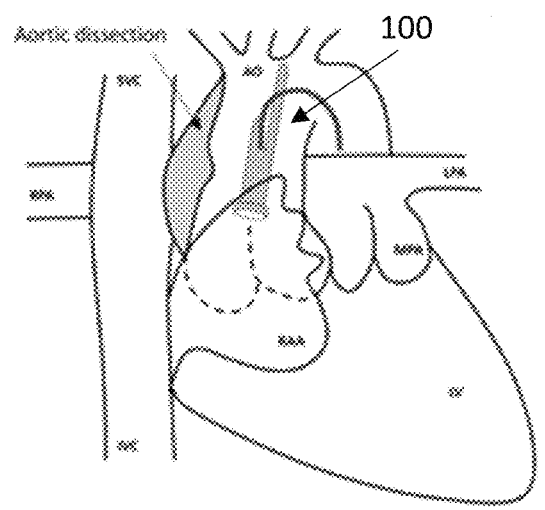
Figure 1E:
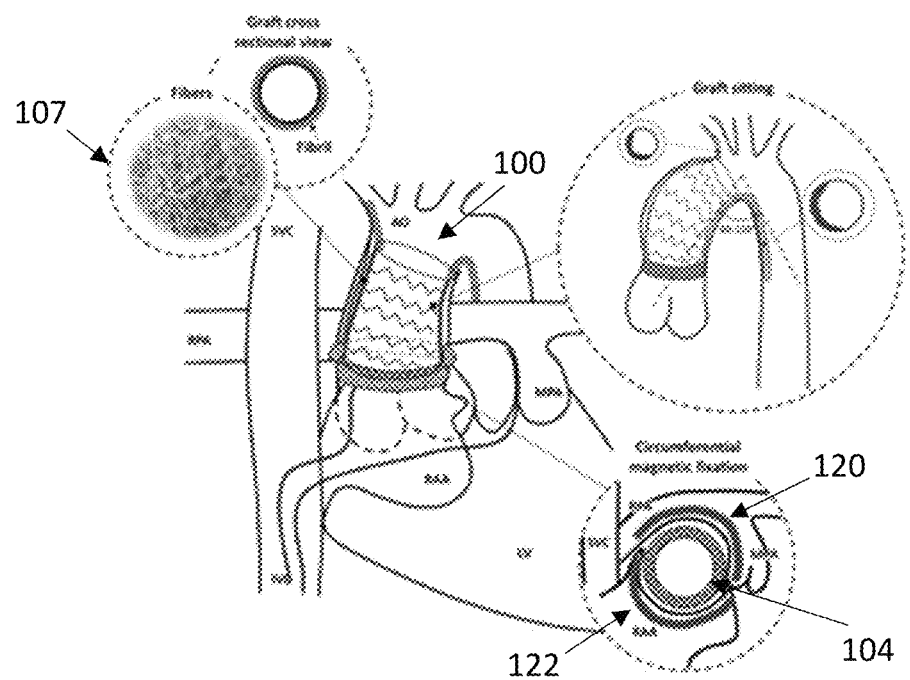
Figure 1F:
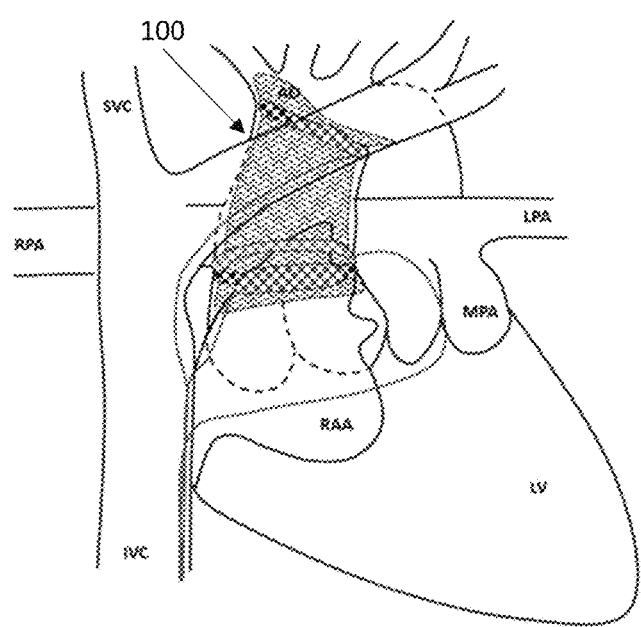
Figure 1G:
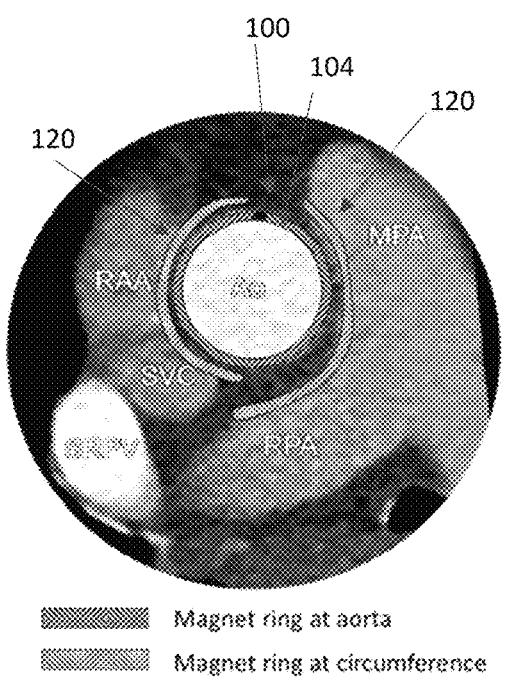

With reference now to FIGS. 1C-1G, a device and system for treating aortic dissection is shown according to one embodiment. The system includes a device 100 having a sinotubular junction magnetic array proximal end with magnets 104, a distal end 106 and an expandable and flexible body 105. The body 105 can include aortic stent graft material or medical grade fibers 107 known in the art for repairing tissue, tears and other structures in and around the heart. The magnetic array 104 has a first plurality of magnetic elements and the system can include a counter-magnetic array 120, 122 having a second and third plurality of magnetic elements. The magnets can be any series or array of magnets, which may include 2, 3, 4, 5, 6, 7, more magnets. The magnets can be the same or an increasing or decreasing variable size, and different geometries of magnets can be used, for example square, rectangular or circular. The magnets can be aligned or offset in two or more rows in certain embodiments. In one embodiment, the poles of the first plurality of magnetic elements are configured to correspond with the poles of the second and third plurality of magnetic elements to implement circumferential magnetic fixation as illustrated in FIG. 1E. Advantageously, the magnetic forces can be utilized to expand the device 100 and fixate the graft material at the treatment site. In one embodiment, sinotubular junction magnetic array is a ring. In one embodiment, the ring is a multi-component ring. In one embodiment, the counter-magnetic array is a ring. In one embodiment, the ring is a multi-component ring. In one embodiment, the ascending aortic stent graft comprises a first and second extension wing. As shown in FIG. 1C, the extension wings can include a descending wing 102 and an innominate wing 108. The device can be advanced through a delivery catheter or sheath 110 and over a guidewire to access the target treatment site.

Figure 2:
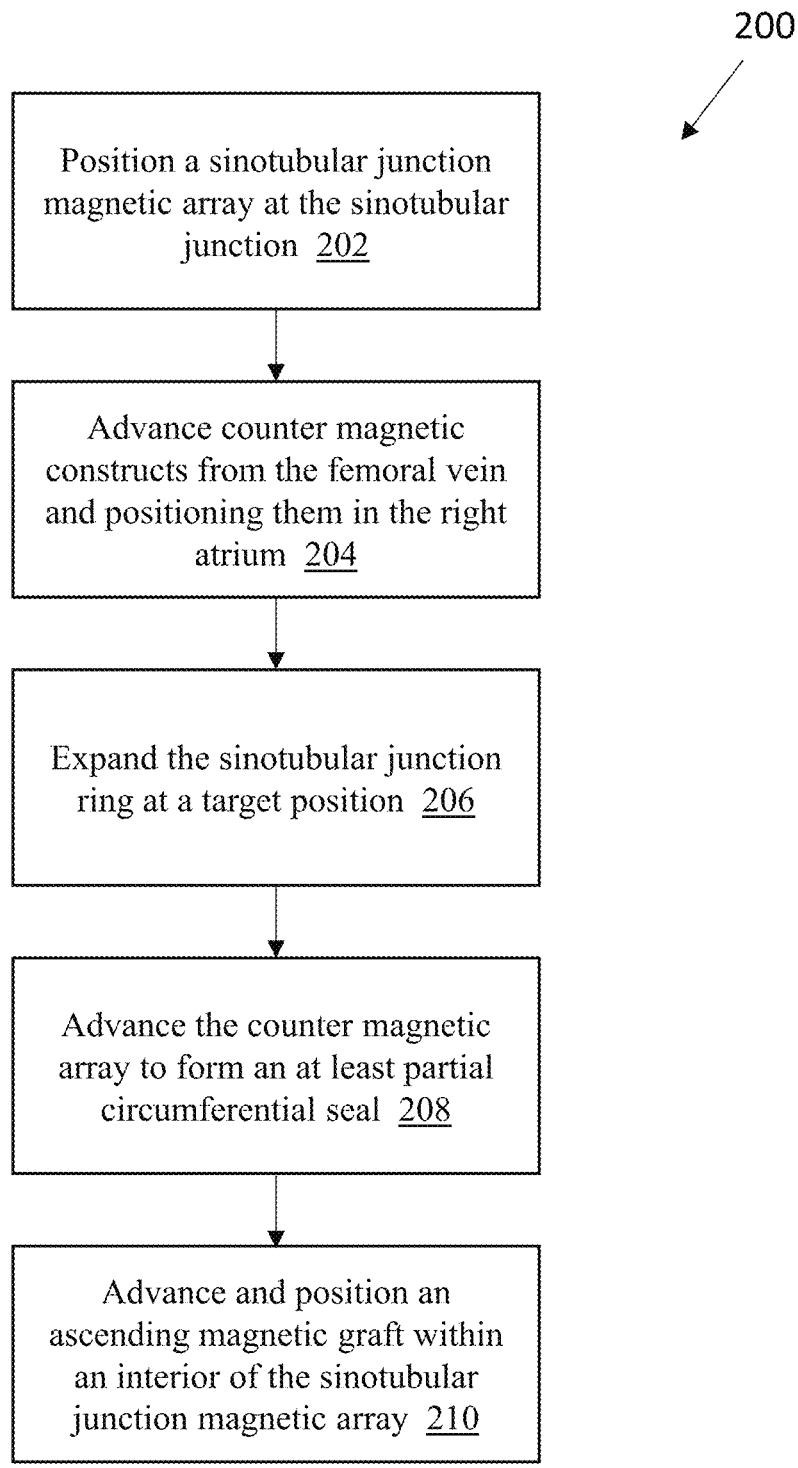
FIG. 2 is a flow chart of a method for treating aortic dissection according to one embodiment.

With reference now to FIG. 2, a method for treating aortic dissection is shown according to one embodiment. The method includes the steps of positioning a sinotubular junction magnetic array at the sinotubular junction 202; advancing counter magnetic constructs from the femoral vein and positioning them in the right atrium 204; expanding the sinotubular junction ring at a target position 206; advancing the counter magnetic array to form an at least partial circumferential sea 208I; and advancing and positioning an ascending magnetic graft within an interior of the sinotubular junction magnetic array.

More specifically, a method of delivering the device to the target location includes the following steps according to one embodiment:

(1) Micropuncture access to right and left femoral vein and arteries and left brachial artery and cephalic vein, dilate the tract and inset 5 Fr sheaths;

(2) Advance a 0035 guidewire to true lumen and pass retrogradely via aortic valve into the left ventricular lumen;

(3) Via left brachial guidewire and catheter, perform an aortogram by placing the pigtail guidewire in the non-coronary cusp (this will help with delineation and measurements of the aorta and extent of the dissection and needed graft length and diameter);

(4) Access right IJ for an intracardiac echocardiogram;

(5) Advance after dilation a catheter assembly with a preloaded crimped sinotubular junction ring from the right femoral artery and position it at the sinotubular junction of the diseased aorta;

(6) Advance counter magnetic constructs from the femoral vein and position them in the right atrium without yet deploying;

(7) Expand the sinotubular junction ring which has magnetic poles to the desired position, advance the counter magnetic array from the right atrial catheter delivery assembly and sectors the ring in 360 degrees by first fixing the four diametrically opposite sites for stability, and at this stage the sinotubular junction ring can be fully released from the delivery sheath;

(8) Continue to apply further counter magnetic Arrays to get a good circumferential seal, check with an aortogram (digital subtraction);

(With this first maneuver the aortic valve continuity and competence will be established)

(9) Exchange the STJ ring sheath now for the ascending aortic stent graft which has magnetic constructs incorporated within its walls as described in figures;

(10) Choose an appropriate size and diameter which will fit within the STJ ring construct, this will be the proximal fixation;

(11) Position the ascending magnetic (MagnaFix) graft and advance within the interior ring of STJ ring constructs, slowly deploy as the delivery sheath is withdrawn and MagnaFix is deployed;

(12) The MagnaFix can have additional fixation or extension flares that can extend in to the brachiocephalic artery and arch and descending aorta (and may include a shape memory material to assume the correct orientation;

(13) From the right atrium start applying counter magnetic constructs as needed to get a good circumferential seal, additional magnetic counter constructs can be deployed from the cephalic vein and advanced to the brachicephqlic vein to apply counter magnetic forces;

(14) Introduce cardiac echo to help get additional imaging; and

(15) Once the system is in place the catheters and sheaths are withdrawn after final aortogram and hemostasis is obtained.

Figure 3A:
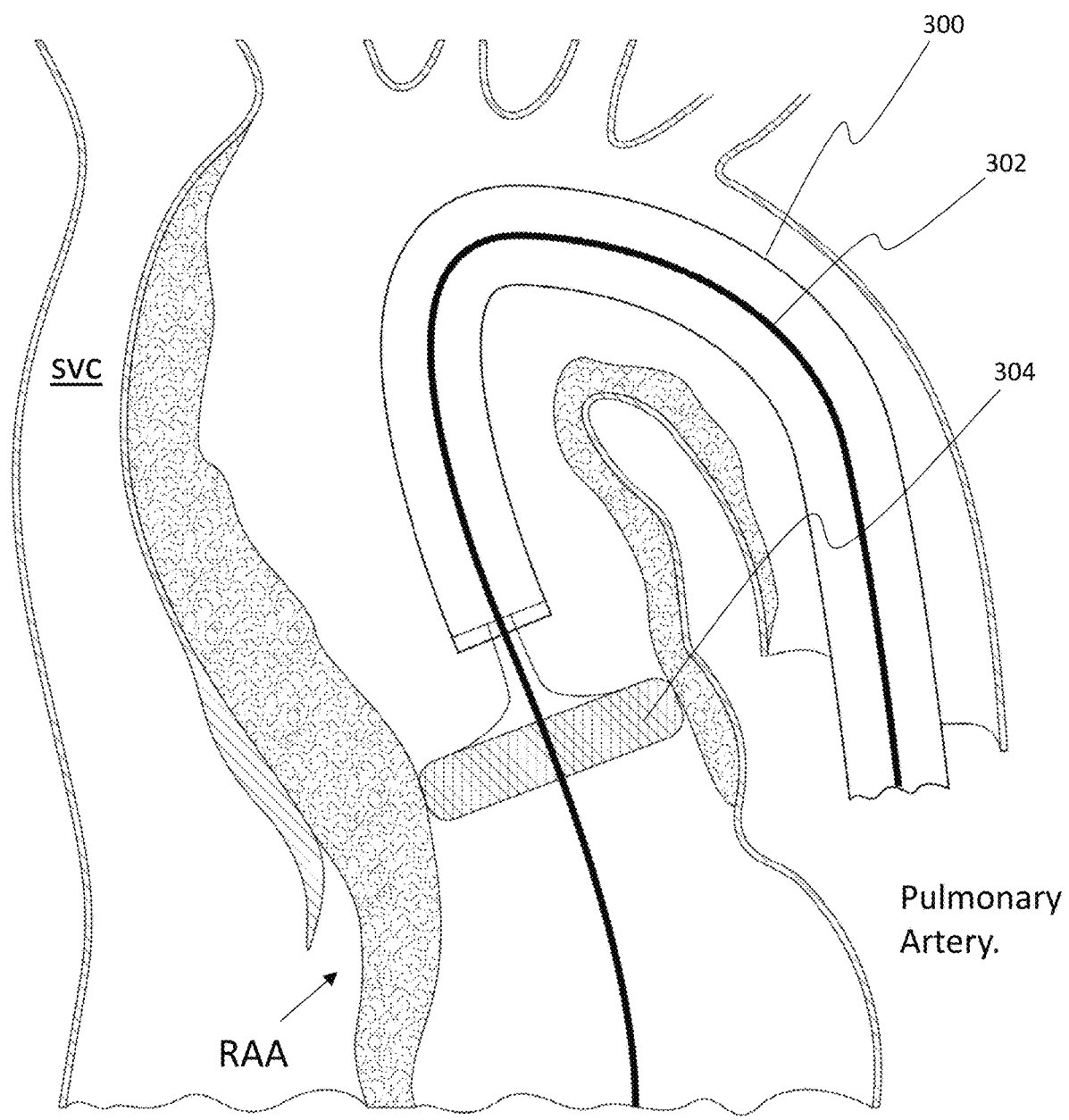
FIG. 3A is a functional view of advancement of a sinotubular junction ring to the sinotubular junction.
Figure 3B:
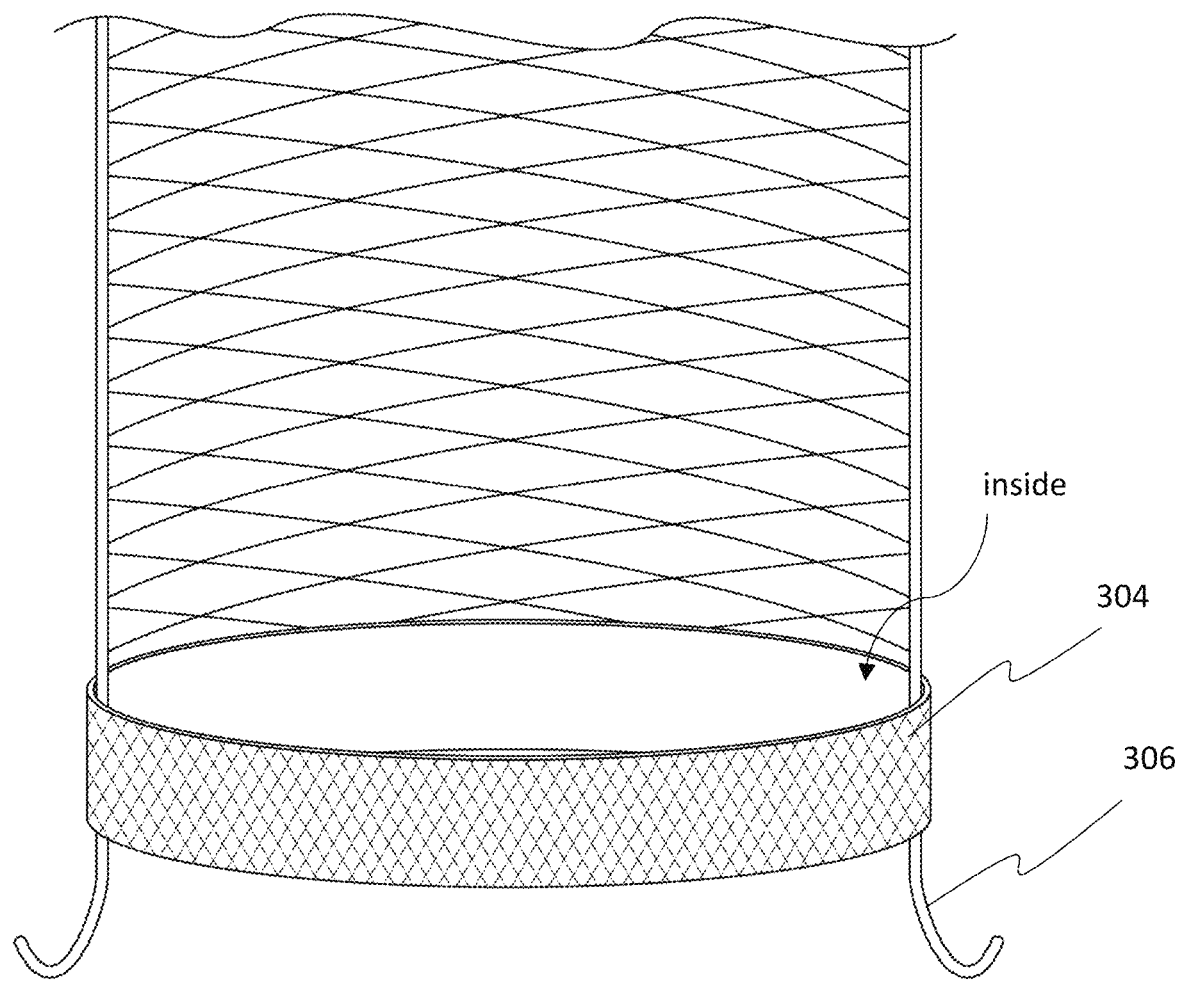
FIGS. 3B and 3C are functional views showing a sinotubular junction ring structure and positioning relative to venous wall, counter array and stent, and FIG. 3D deployment of sheath, according to one embodiment.
Figure 3C:
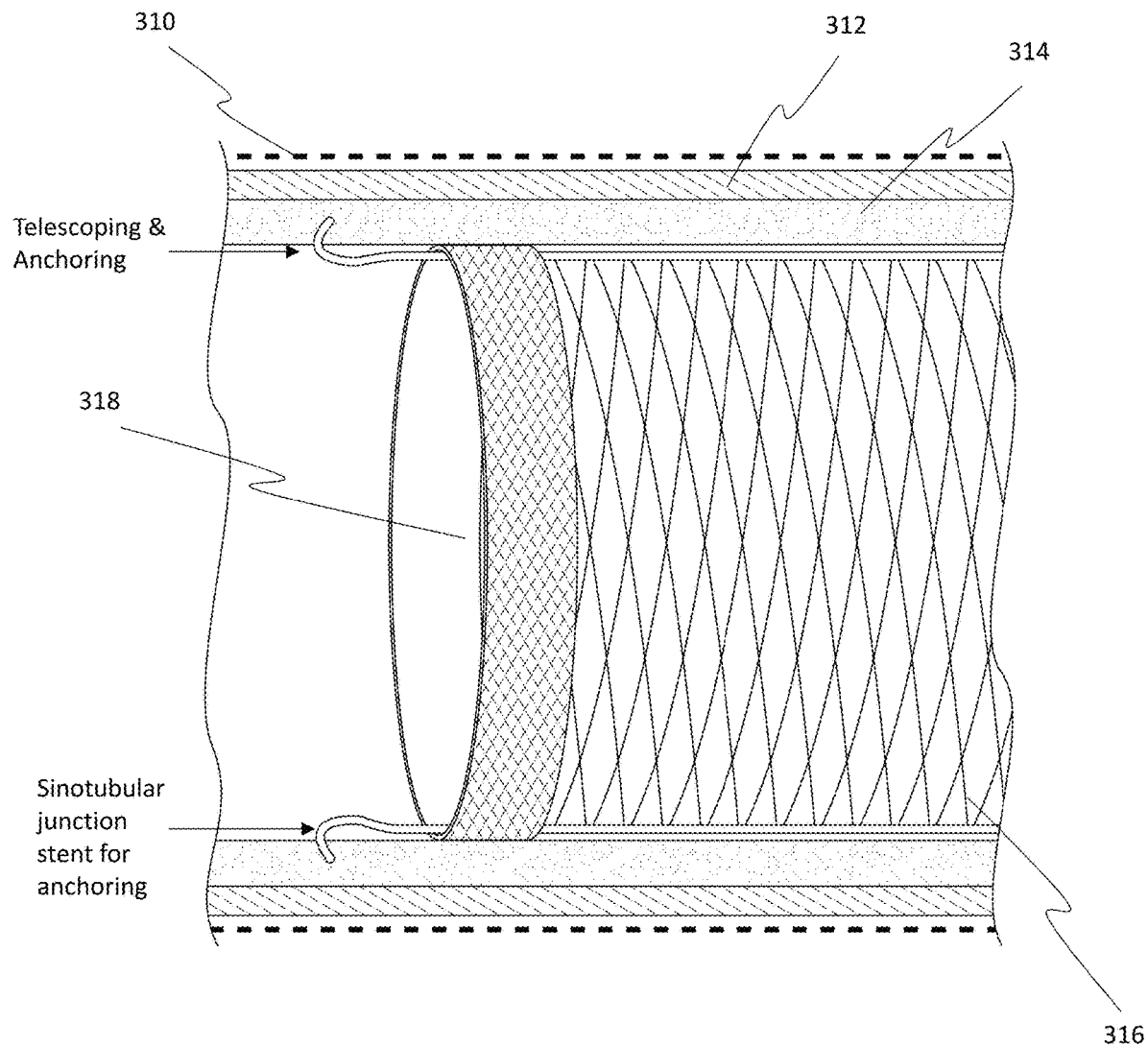
Figure 3D:
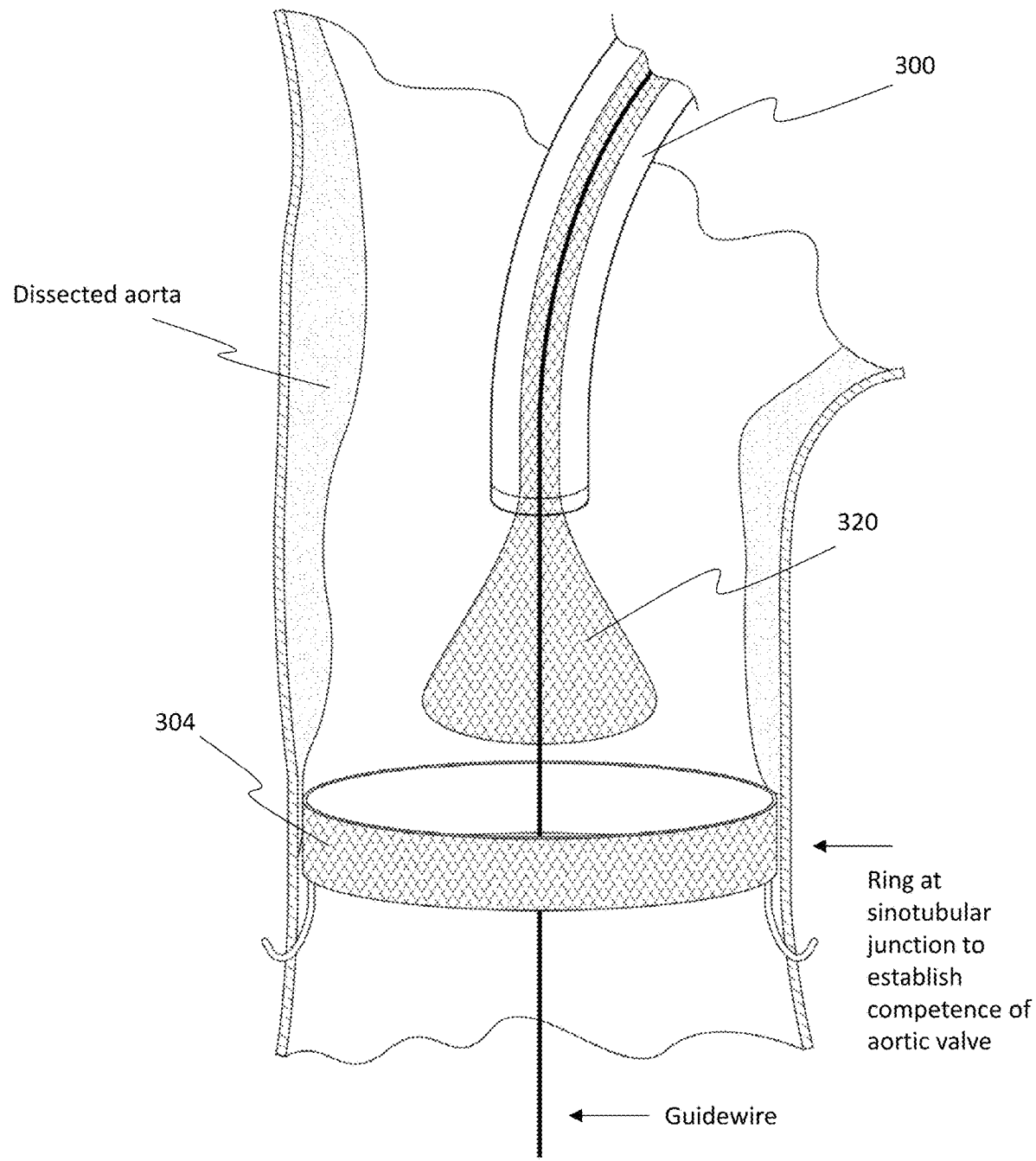

With reference now to FIGS. 3A-3D, a method for treating aortic dissection is illustrated according to one embodiment. With reference to FIG. 3A, advancement of sinotubular junction ring to the sinotubular junction is illustrated. A sheath 300 is shown coaxially surrounding the device with the magnetic ring 304 partially deployed, both the sheath 300 and the magnetic ring 304 loaded over a guidewire 302. With reference to FIGS. 3B and 3C, the sinotubular junction ring structure and positioning relative to venous wall, counter array and stent is shown. Adjacent to the ring 304 can be one or more anchors 306, in one embodiment soft anchors for fixing a target position. The anchors 306 can in one embodiment set into the dissected arterial wall 314 so that the stent 316 provides patency for the arterial lumen 308, and the magnetic array 310 and stent 316 sandwiches the venous wall 312 and dissected arterial wall 314 (see FIG. 3C). The deployment of the graft 320 from the sheath 300 adjacent to the dissected aorta (see FIG. 3D) is facilitated by the magnetic properties of the graft and the ring placement at the sinotubular junction to establish aortic valve competency.

Figure 4A:
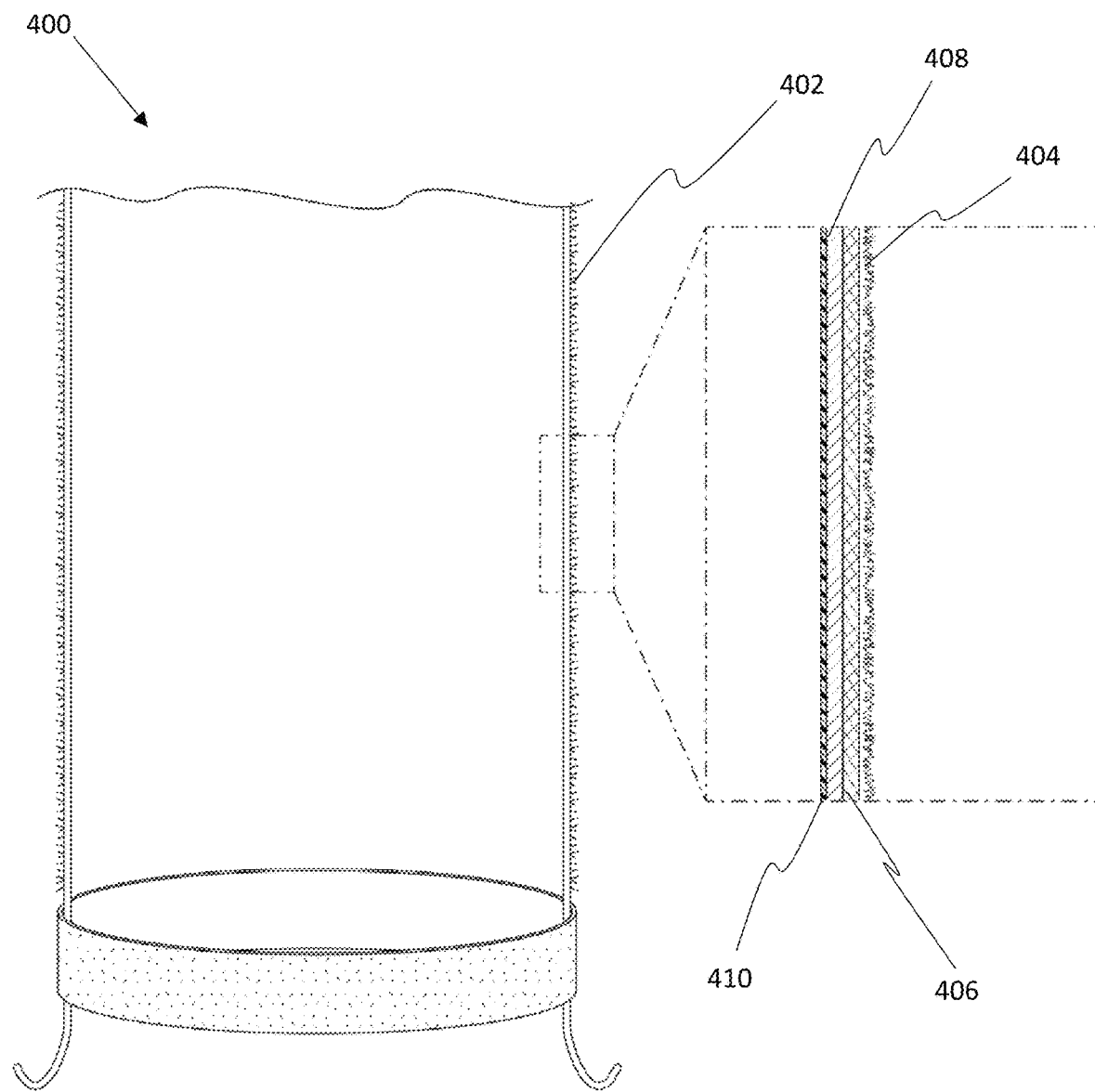
FIG. 4A is a side and cutaway view of anchoring mechanisms and device layers.
Figure 4B:
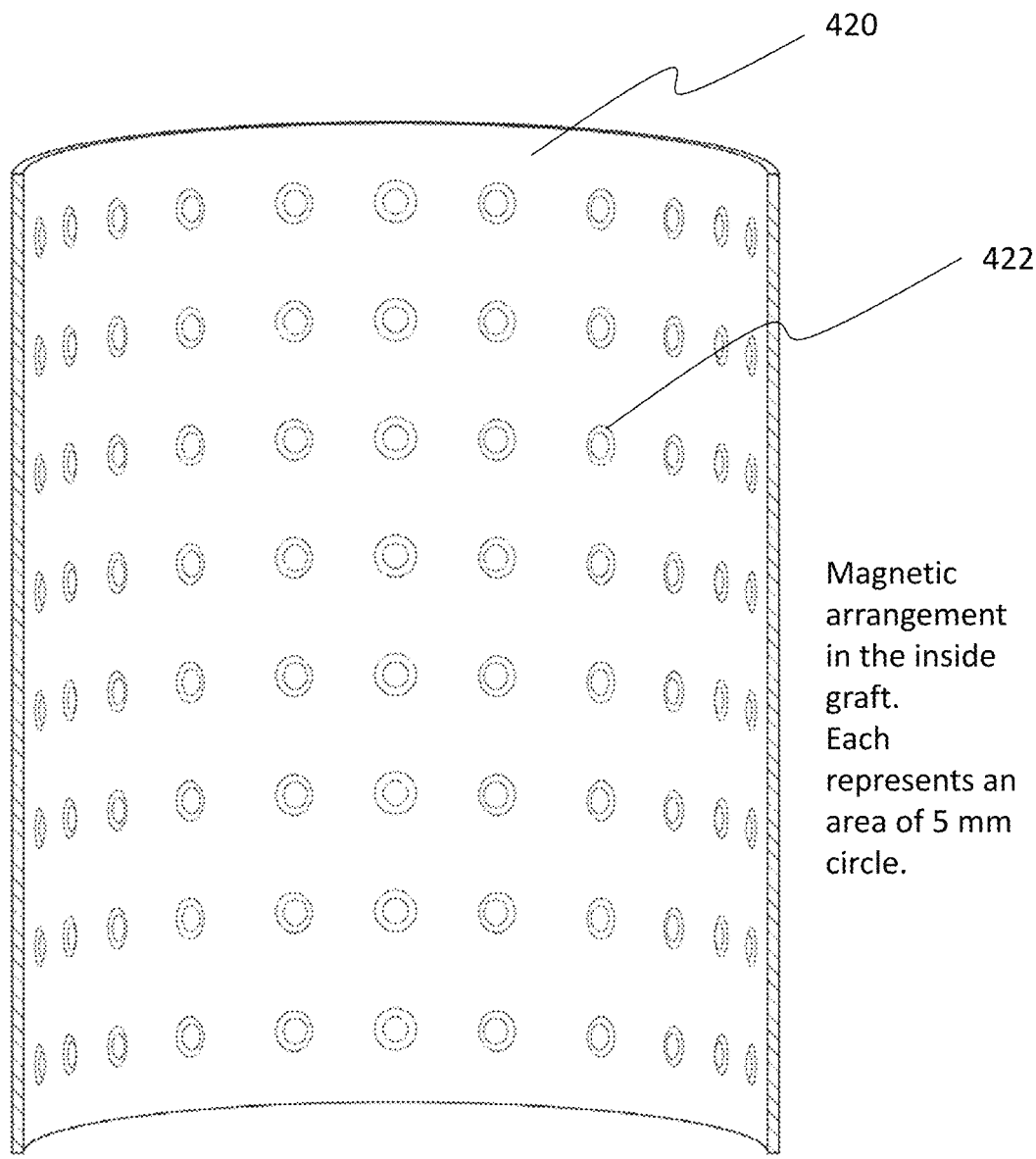
FIG. 4B is a side view of a sample magnetic array inside a graft.
Figure 4C:
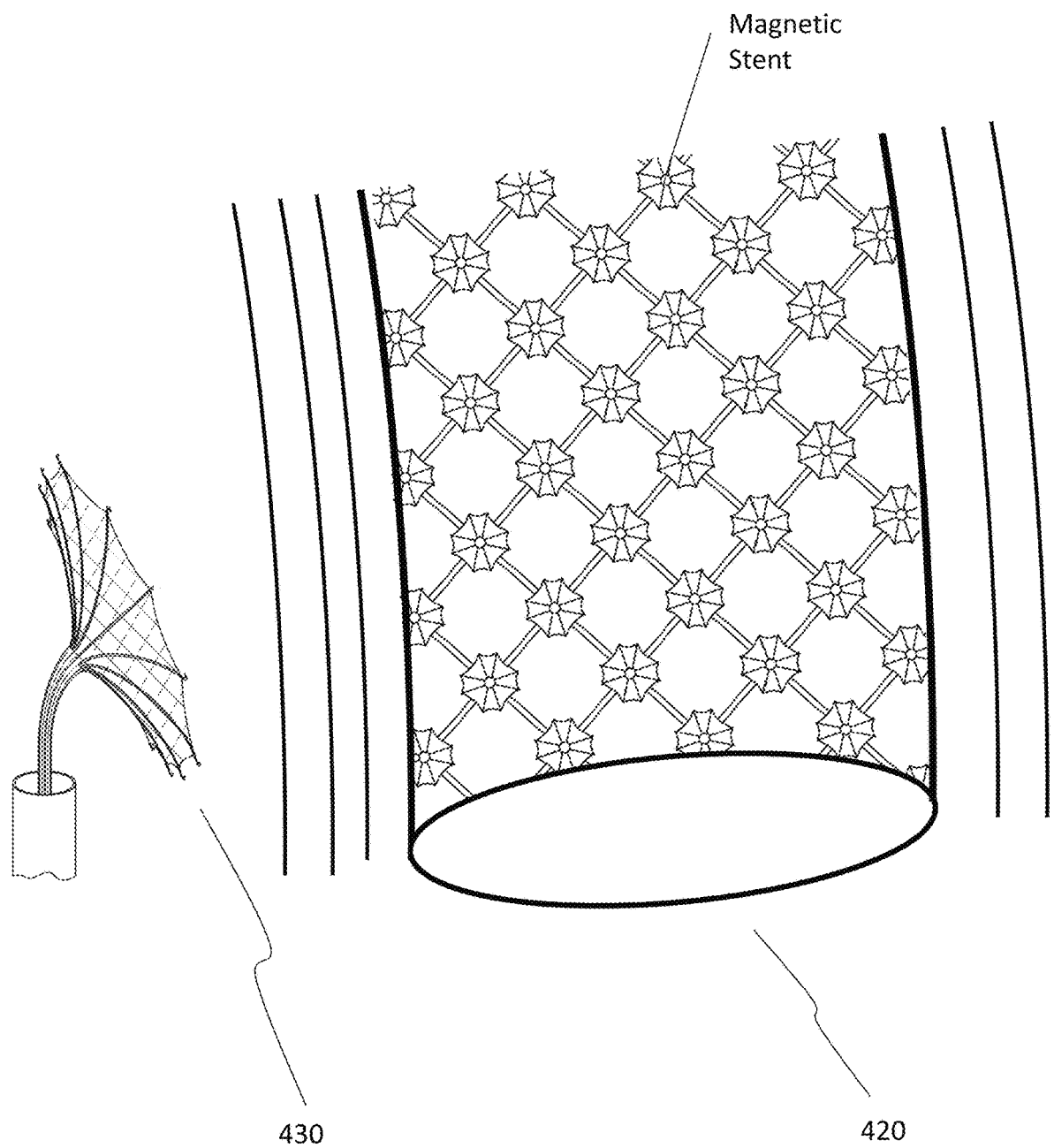
FIG. 4C is a functional view of positioning opposing magnetic array for holding a stent in place.
Figure 4D:
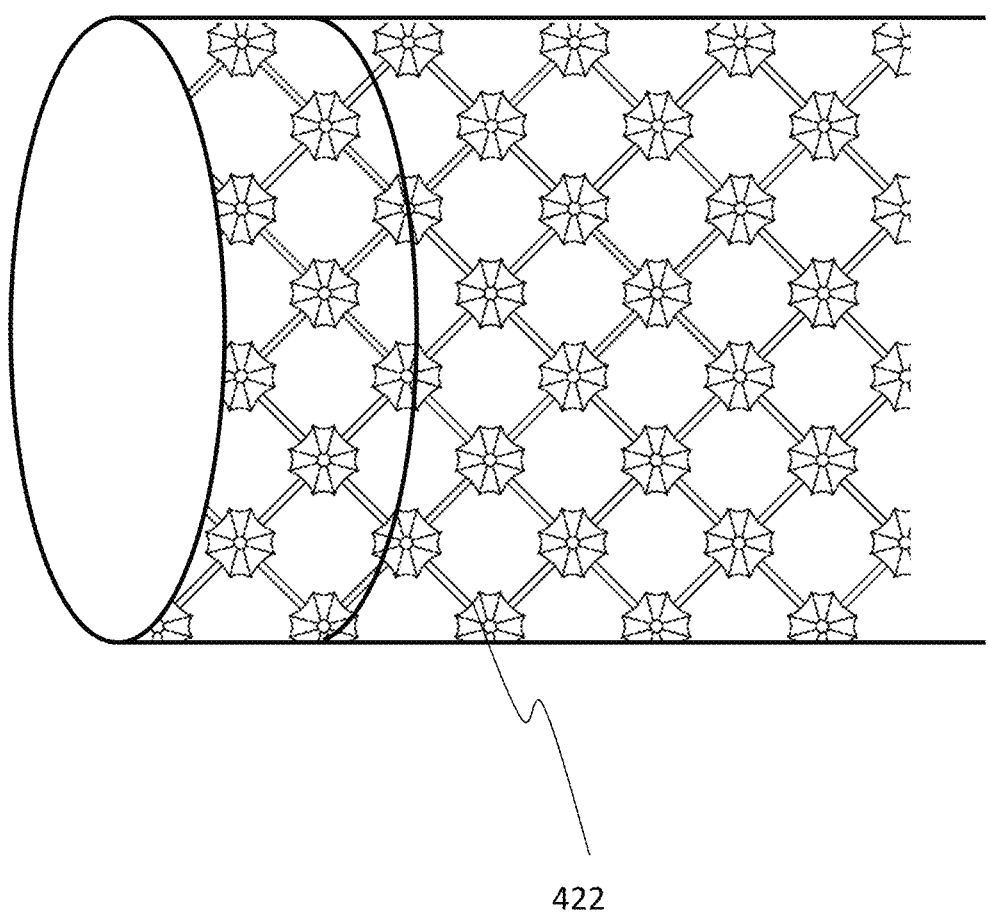
FIGS. 4D and 4E are side views of magnetic pole structure can be held by shape memory alloy to deploy into the desired geometry.
Figure 4E:
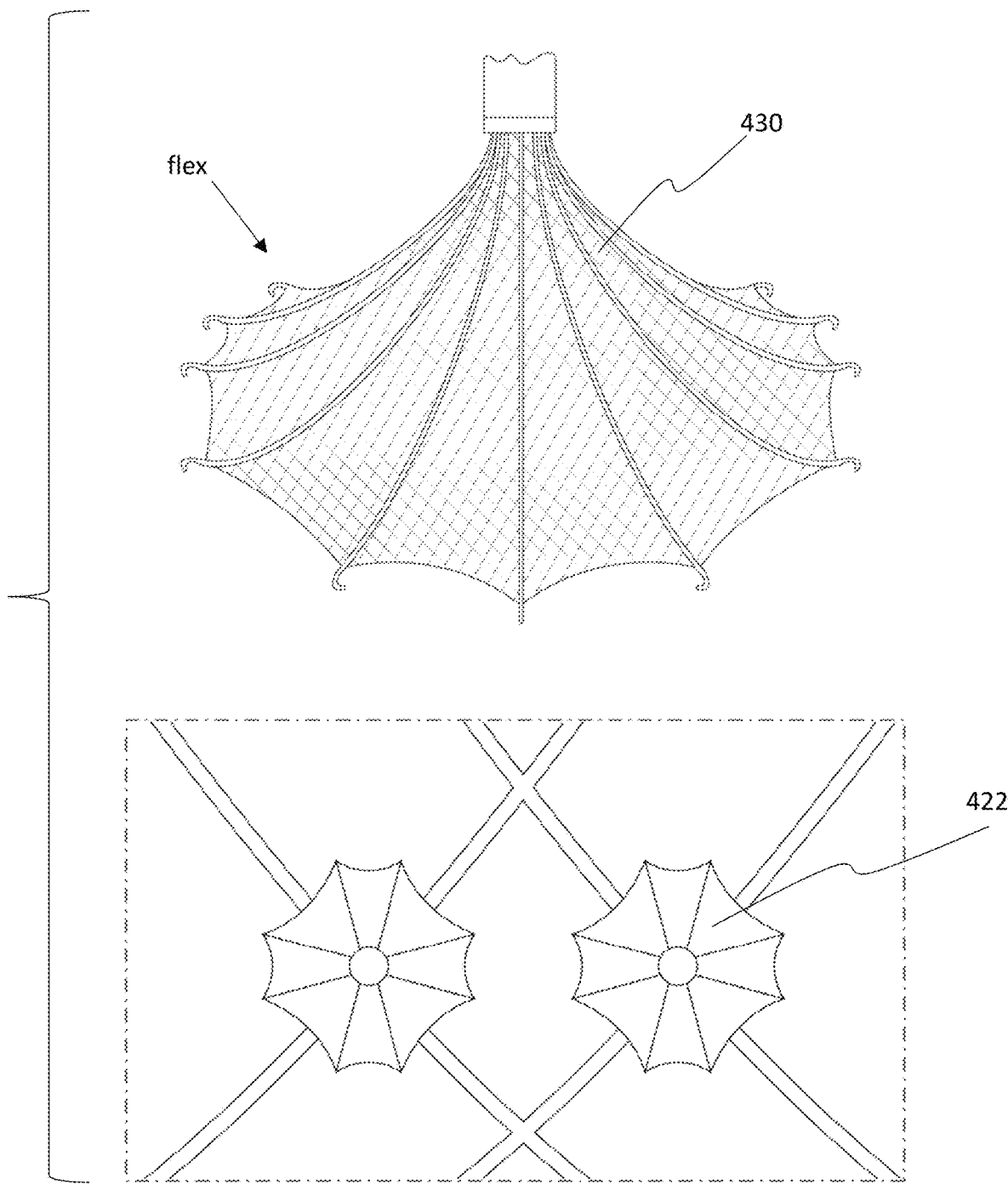

With reference now to FIGS. 4A-4E, magnified views of the stent layers are shown according to one embodiment. With reference to FIG. 4A, a stent 400 structure includes an exterior layer of soft fibrils 402 to encourage attachment to the treatment site and full device anchoring over time. The fibril material 402 can be for example Dacron, polyester or polytetrafluoroethylene. The fibrils 402 are disposed on a PTFE layer 404, which is next to the magnetic material layer 406. A stainless steel scaffold layer 408 sits adjacent to the internal layer of PTFE layer 410. It will be appreciated by those having ordinary skill in the art that the layers described herein can be substituted for a similar medical grade material known in the art. With reference to FIGS. 4B-4E, arrangements of magnetic elements are shown according to one embodiment. The magnetic elements 422 can be disposed on a single layer 420, and in one embodiment are disposed on cross-sections of a scaffold layer. A deployment element 430 can be utilized that attracts opposing magnetic poles for holding the stent in place and adjusting its position.

Figure 5A:
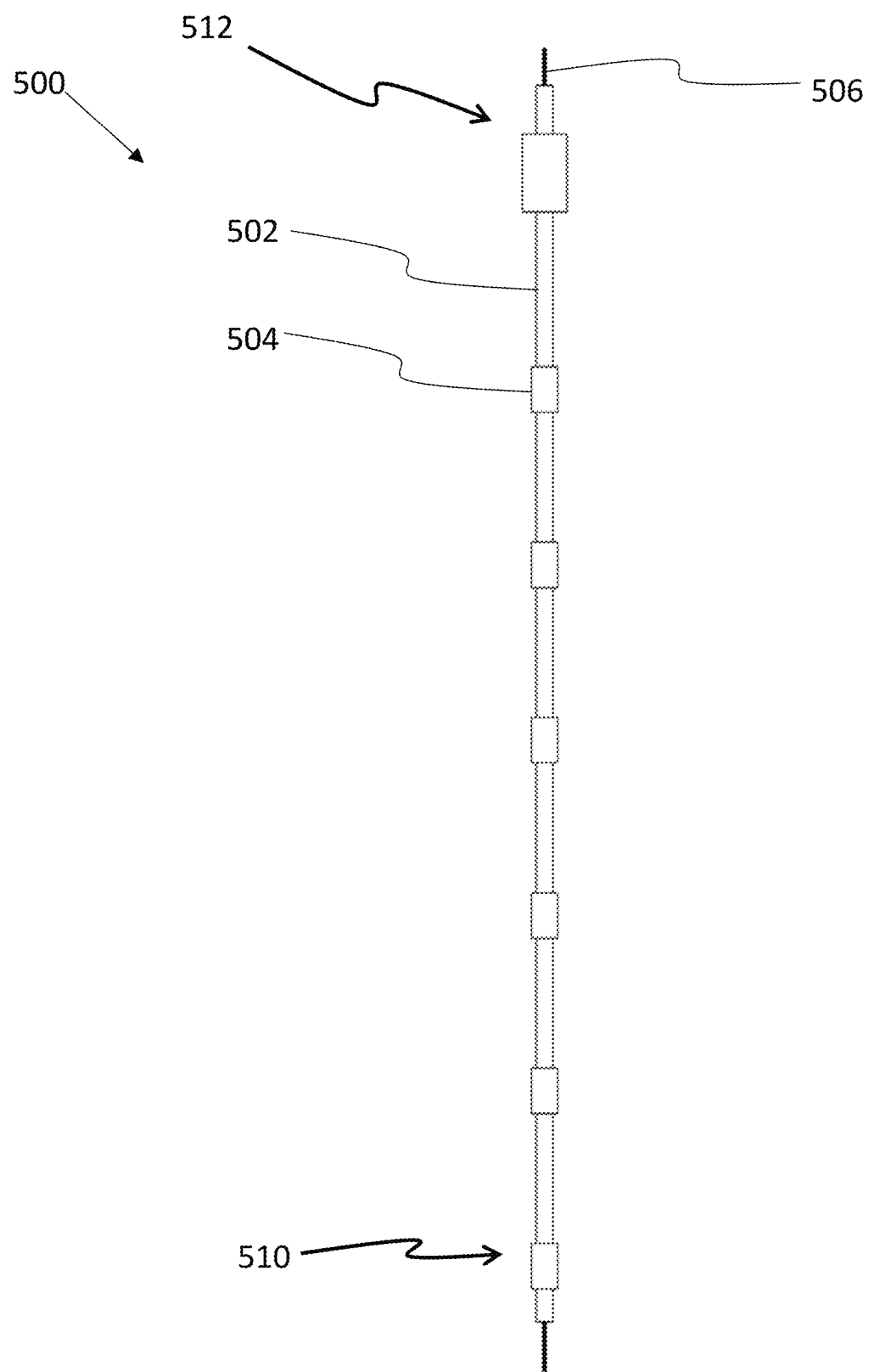
FIG. 5A is a side view of a stacked helical device for treating aortic dissection.
Figure 5B:
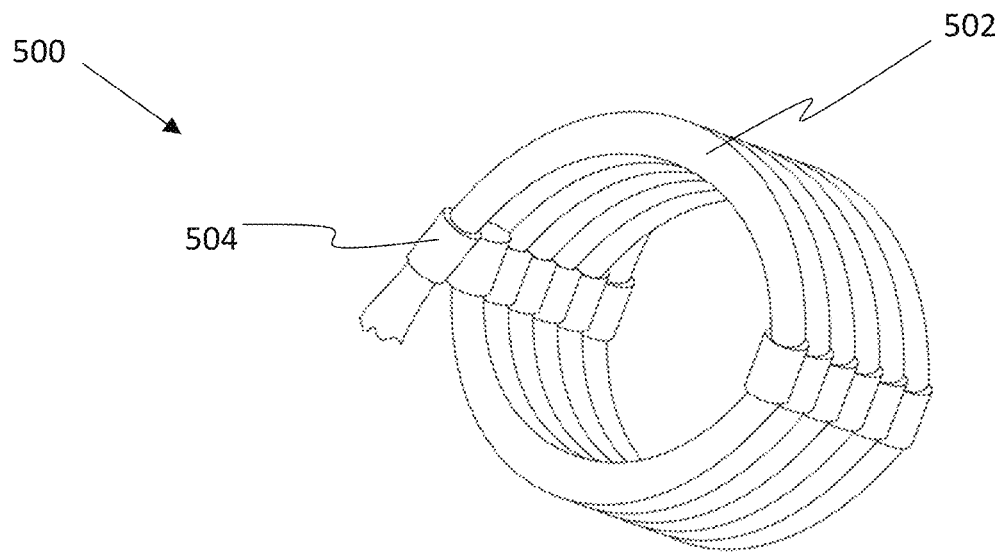
FIGS. 5B and 5C are alternate perspective views of a stacked helical device for treating aortic dissection.
Figure 5C:
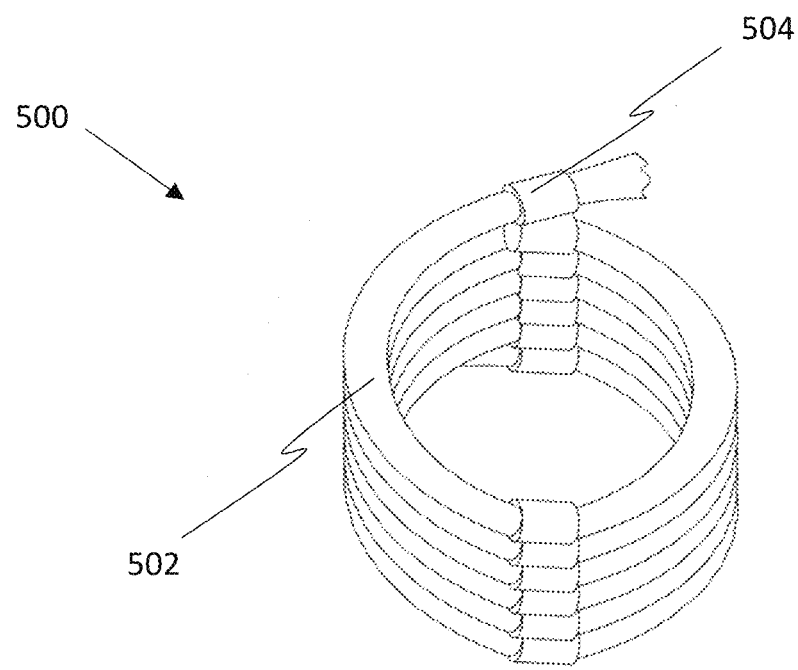
Figure 5D:
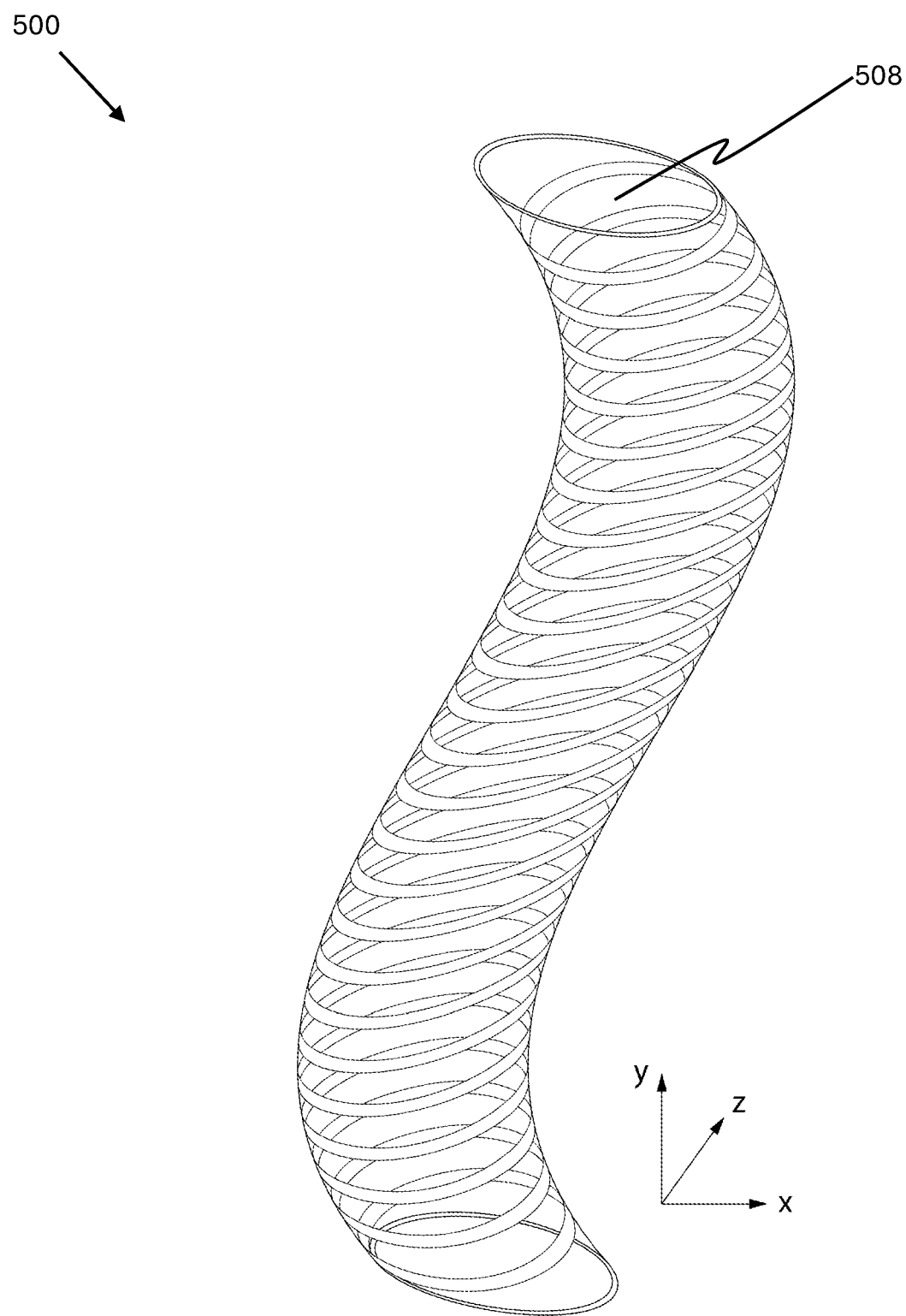
FIG. 5D is a side functional view of a stacked helical device for treating aortic dissection, according to one embodiment.
Figure 6:
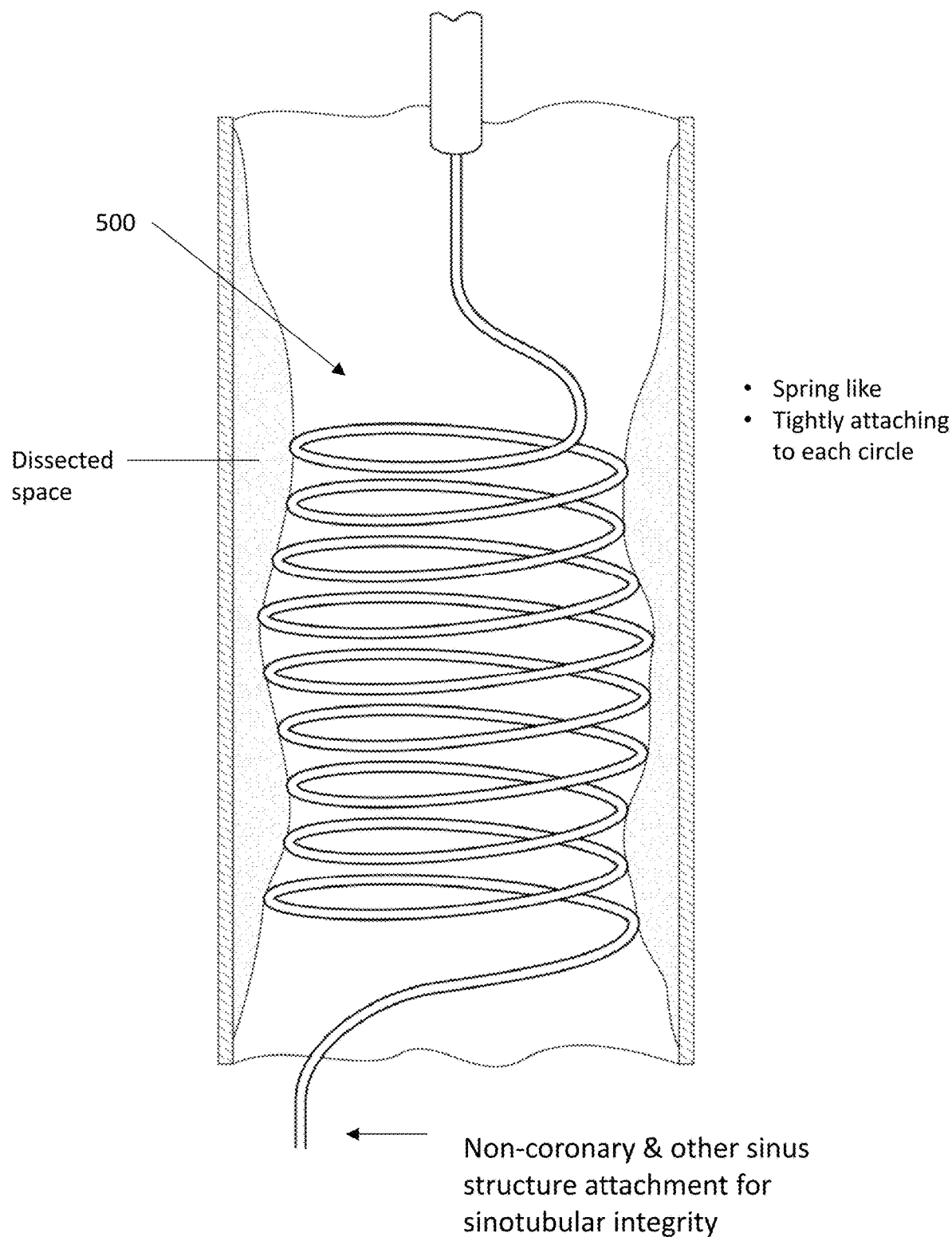
FIG. 6 shows a functional view of a stacked helical device for treating aortic dissection according to one embodiment.

With reference now to FIGS. 5A-5C, according to one embodiment, the device 500 is an elongate device having a proximal end 510 and a distal end 512. The device 500 is generally flexible with a lumen 508 extending therethrough for loading over a guidewire 506, and a series of magnetic elements 504 extended along its length. The magnets can be separated by segments of a medical grade material 502 including those described in previous embodiments for treating damaged tissue. The device 500 can include one or more of a shape memory and magnetic element spacings so that when advances through a sheath the device is elongate (see FIG. 5A), and when deployed from a sheath the device 500 assumes a helical shape (see FIGS. 5B-5D). The magnetic elements 504 can have uniform sizes, variable sizes, uniform spacings or variable spacings. Polarity of adjacent magnets may attract or repel depending on the desired final geometry of the deployed device and how the magnets need to lock together. As shown in FIGS. 5B and 5C, the magnetic element spacings can be used to determine the device diameter upon deployment and can be variable or uniform. The devices can be part of a kit that utilized different helical shapes upon deployment so that after imaging, the correct device is selected by the medical professional based on the patient anatomy and the procedure being performed. Advantageously, as shown in FIG. 5D, embodiments of the device 500 have the flexibility to shift and vary position along the X, Y and Z directions about the central opening 508 to accommodate patient anatomy and fit the plan for treatment. The device can be deployed according to the examples illustrated in FIG. 6 according to one embodiment. The device deploys from a sheath into the target vessel. The device and/or guidewire can have a partial or full shape memory across some or all of its length. The magnets along the length of the device will attract to each other so that as each layer deploys and stacks on top of the previous layer, the device locks into its helical configuration, allowing accommodation along any of the X, Y and Z directions to shift or add variation of cross-sectional profile shape to accommodate patient anatomy.

Figure 7A:
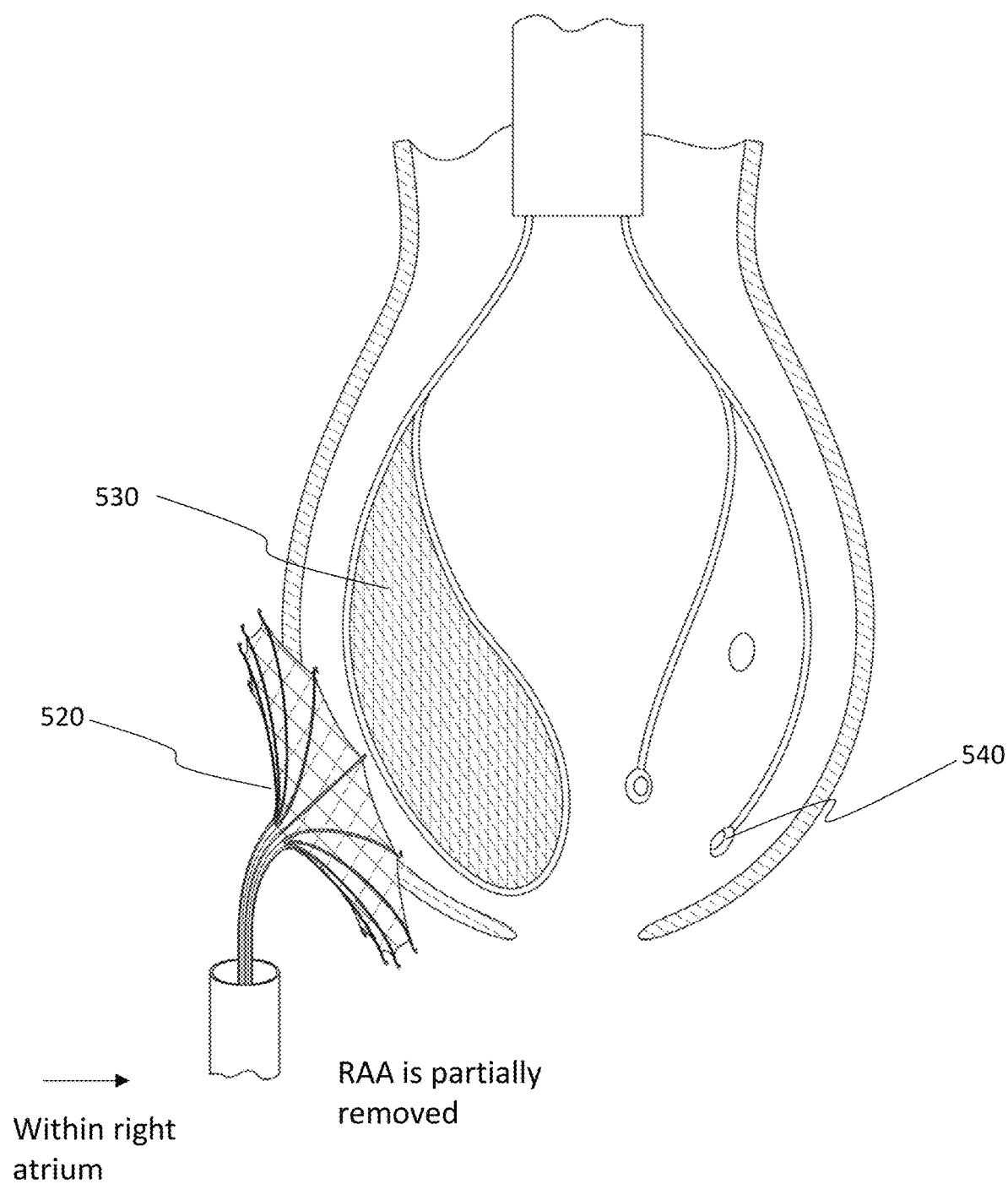
FIG. 7A and 7B show functional views of a fixation device and method according to one embodiment.
Figure 7B:
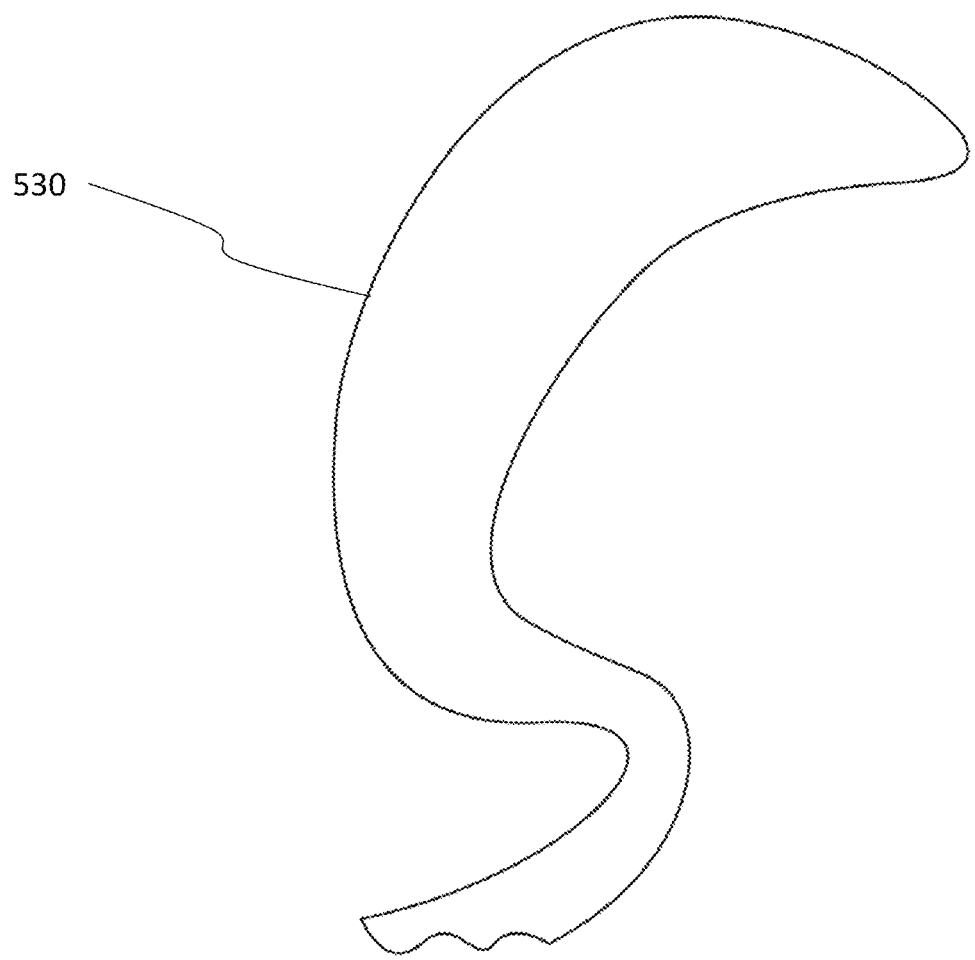

With reference now to FIGS. 7A and 7B, according to one embodiment, a woven nitinol scaffold 530 (cobra headed shape as shown specifically in FIG. 7B) is first inserted to re-establish the integrity of the aortic valve, this is then further reinforced with a catheter that has alternating Dacron covered magnets and silicone tubes to create a spring shaped cylindrical scaffold to support the aortic walls and push the two separated walls together. Counter magnets 520 are used to achieve good blood seal (these counter magnets can be removed in 6 weeks time once the aortic wall has healed). The procedure can be done in a conscious patient under sedation and local anesthesia and can be completed in 30 minutes without need for extensive surgery.

Experimental Examples

The invention is now described with reference to the following Examples. These Examples are provided for the purpose of illustration only and the invention should in no way be construed as being limited to these Examples, but rather should be construed to encompass any and all variations which become evident as a result of the teaching provided herein.

Without further description, it is believed that one of ordinary skill in the art can, using the preceding description and the following illustrative examples, make and utilize the present invention and practice the claimed methods. The following working examples therefore, specifically point out the preferred embodiments of the present invention, and are not to be construed as limiting in any way the remainder of the disclosure.

Figure 8A:
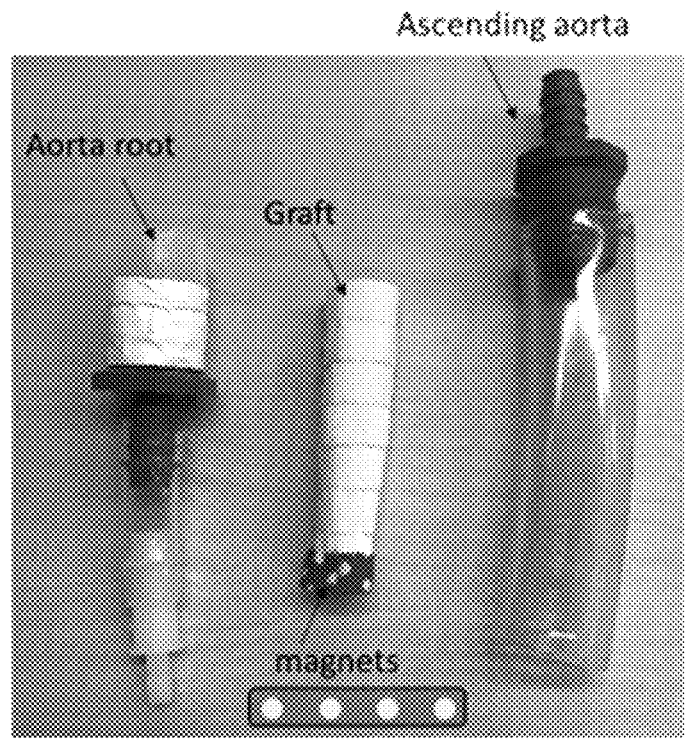
FIGS. 8A-8C show images of an assembly including a prototype aorta root, graft with magnets and ascending aorta.
Figure 8B:
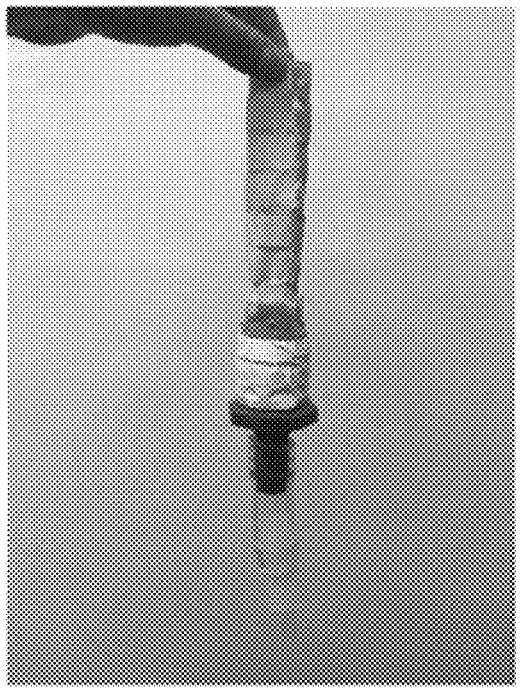
Figure 8C:
Figure 8D:
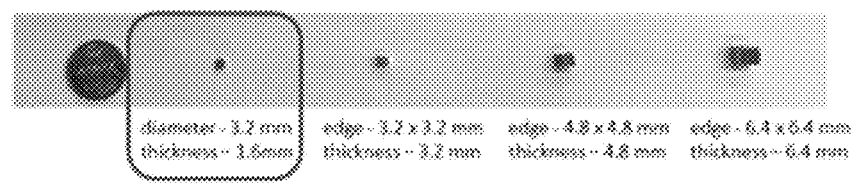
FIG. 8D shows a preferred magnet thickness and FIG. 8E shows a graph of changes in spring constant.
Figure 8E:
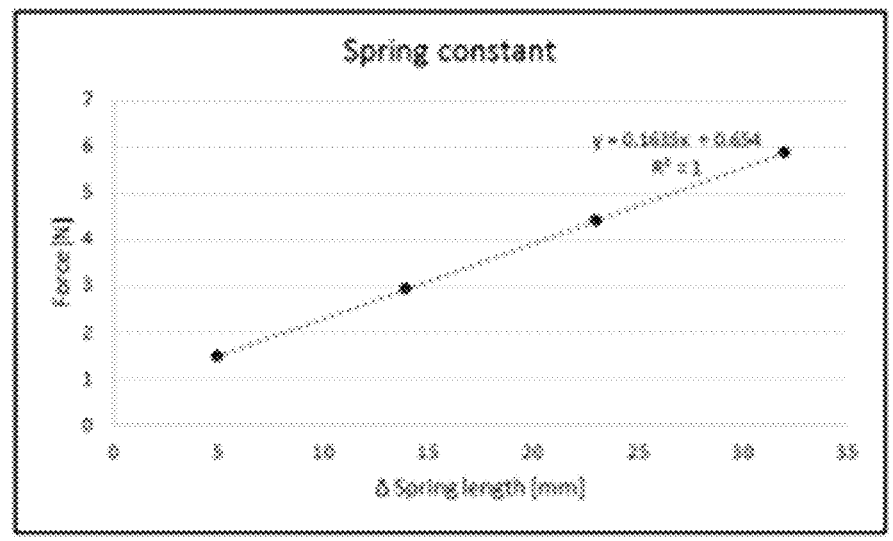
Figure 8F:
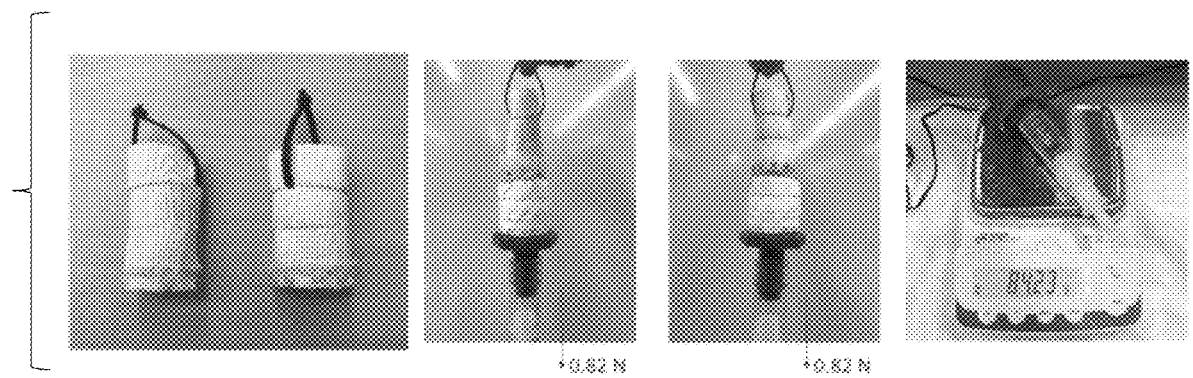
FIG. 8F shows images of an experimental setup for testing magnet configurations.
Figure 8G:
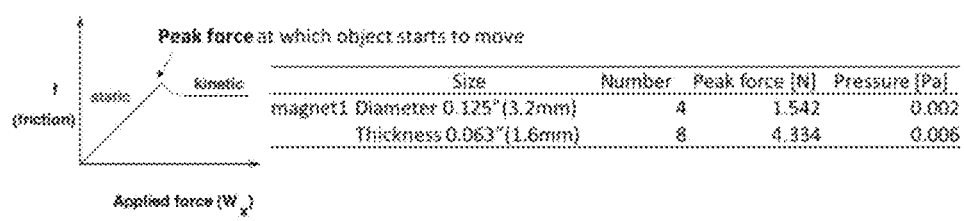
FIG. 8G shows peak force at which the object starts to move and result data for two magnet configurations.
Figures 9A, 9B:
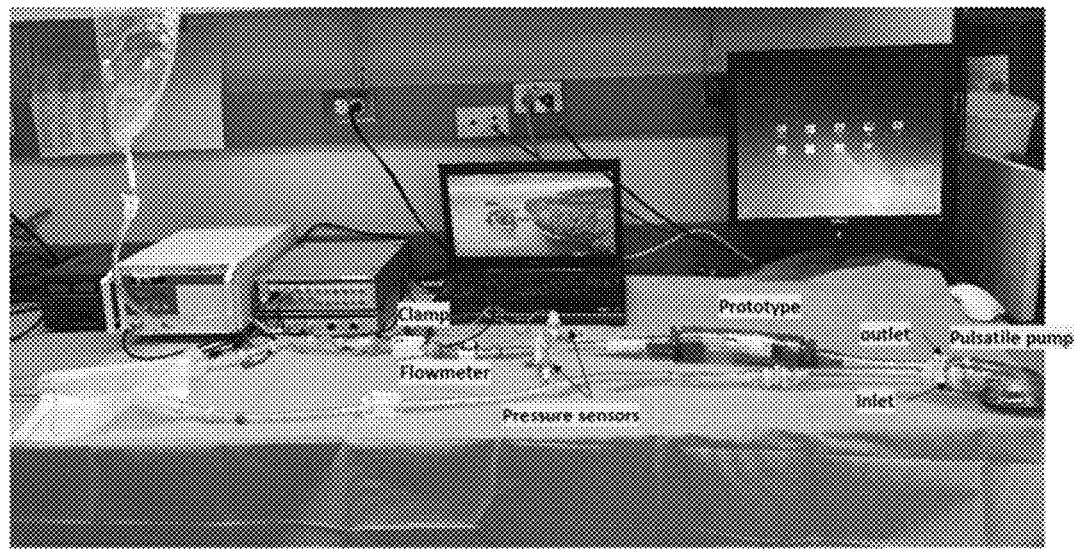
FIG. 9A is an image showing an experimental setup for a pulsatile flow test and FIGS. 9B shows a chart of results for different vacuum pressures and flow rates.
Figure 9C:
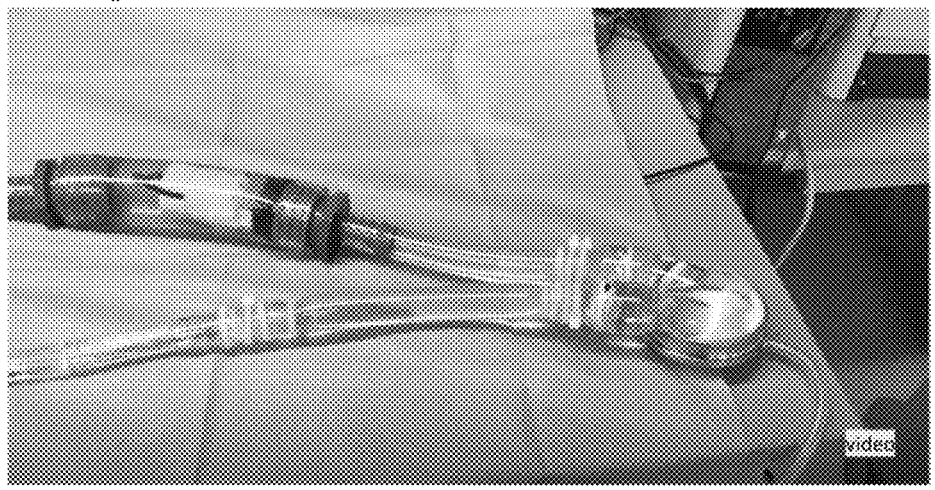
FIG. 9C shows an experimental setup for an 8-magnet configuration at high conditions.
Figure 9D:
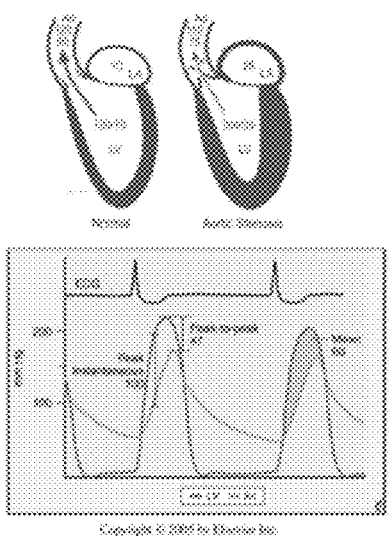
FIG. 9D shows related results data.
Figure 9D:
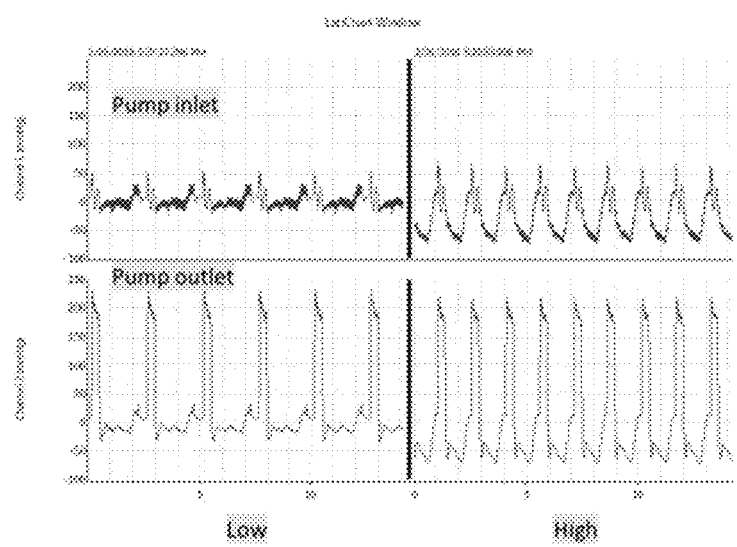
Figure 9E:
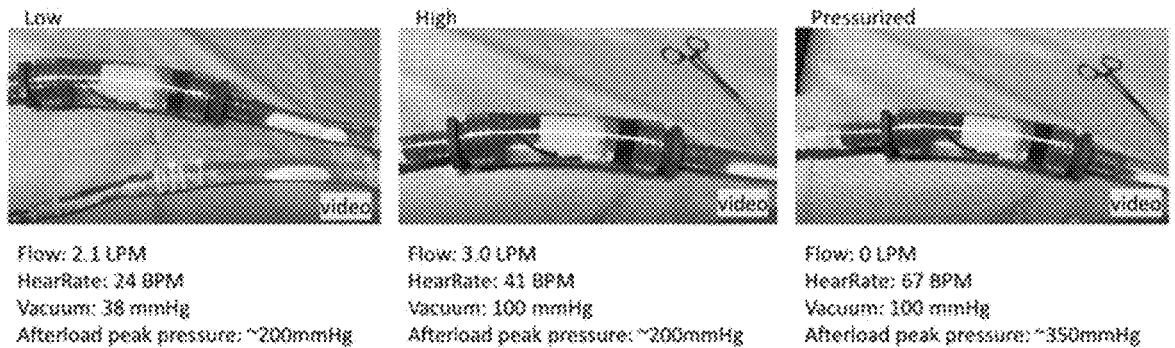
FIG. 9E shows an experimental setup for a 4-magnet configuration at high conditions.
Figure 9F:
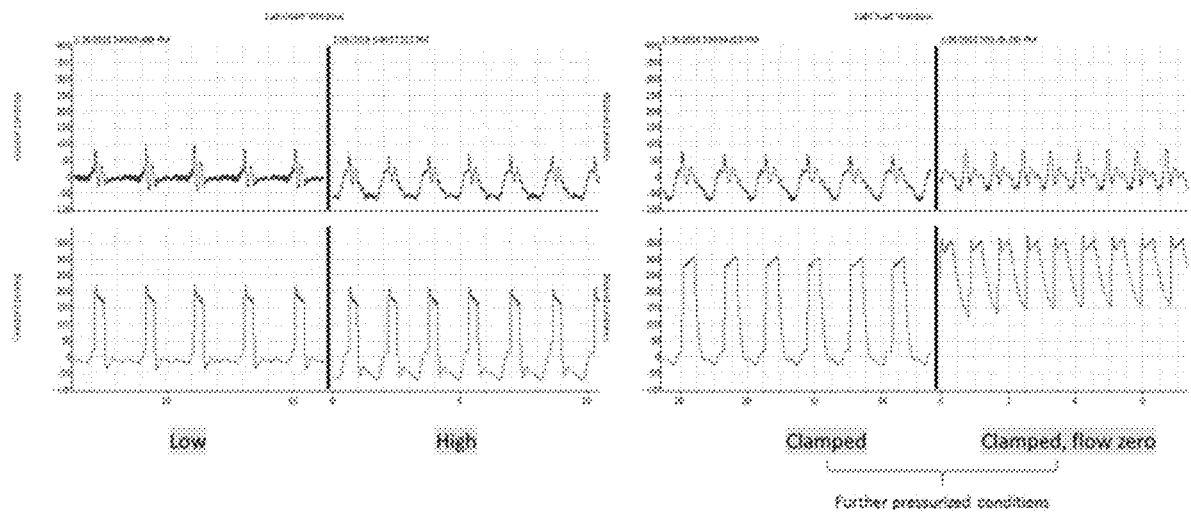
FIG. 9F shows related results data.
Figure 10:
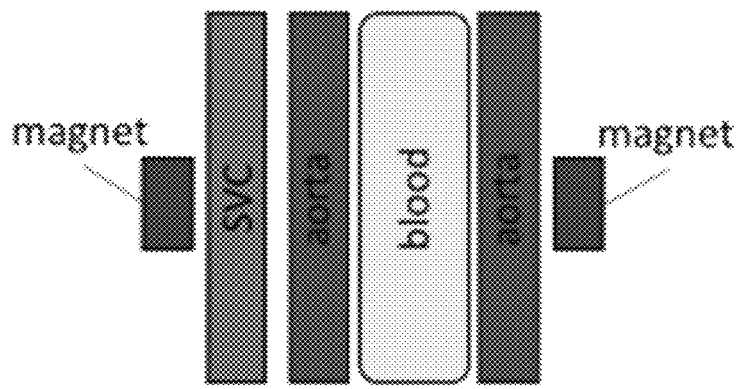
FIG. 10 is a diagram showing an experimental setup and related results data for a magnet test.
Figure 10:
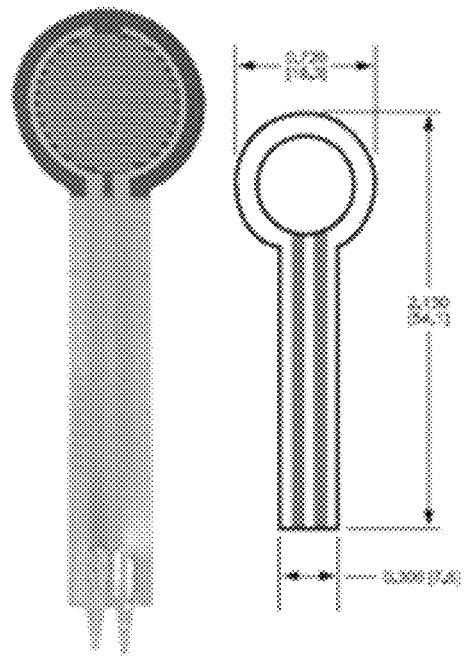
Figure 11A:
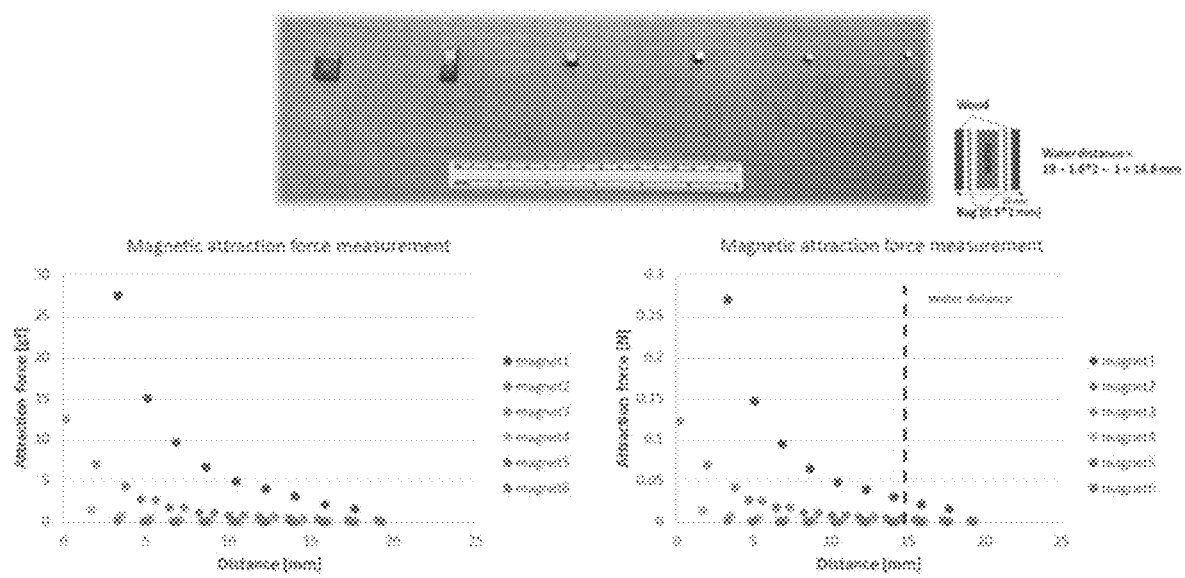
FIG. 11A is an image showing an experimental setup for measuring magnet attraction forces and related results data for different sized magnets.
Figure 11B:
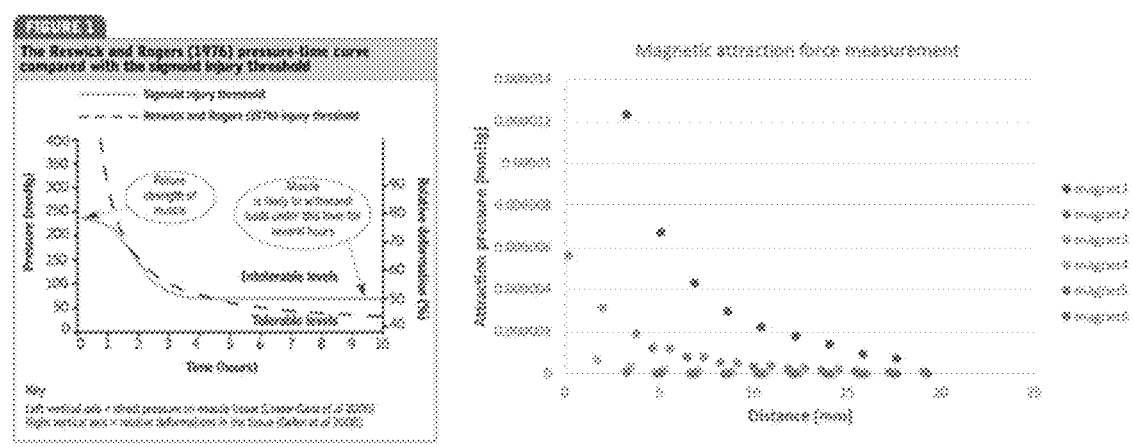
FIG. 11B shows magnetic attraction force measurement data for different sized magnets.
Figure 12:
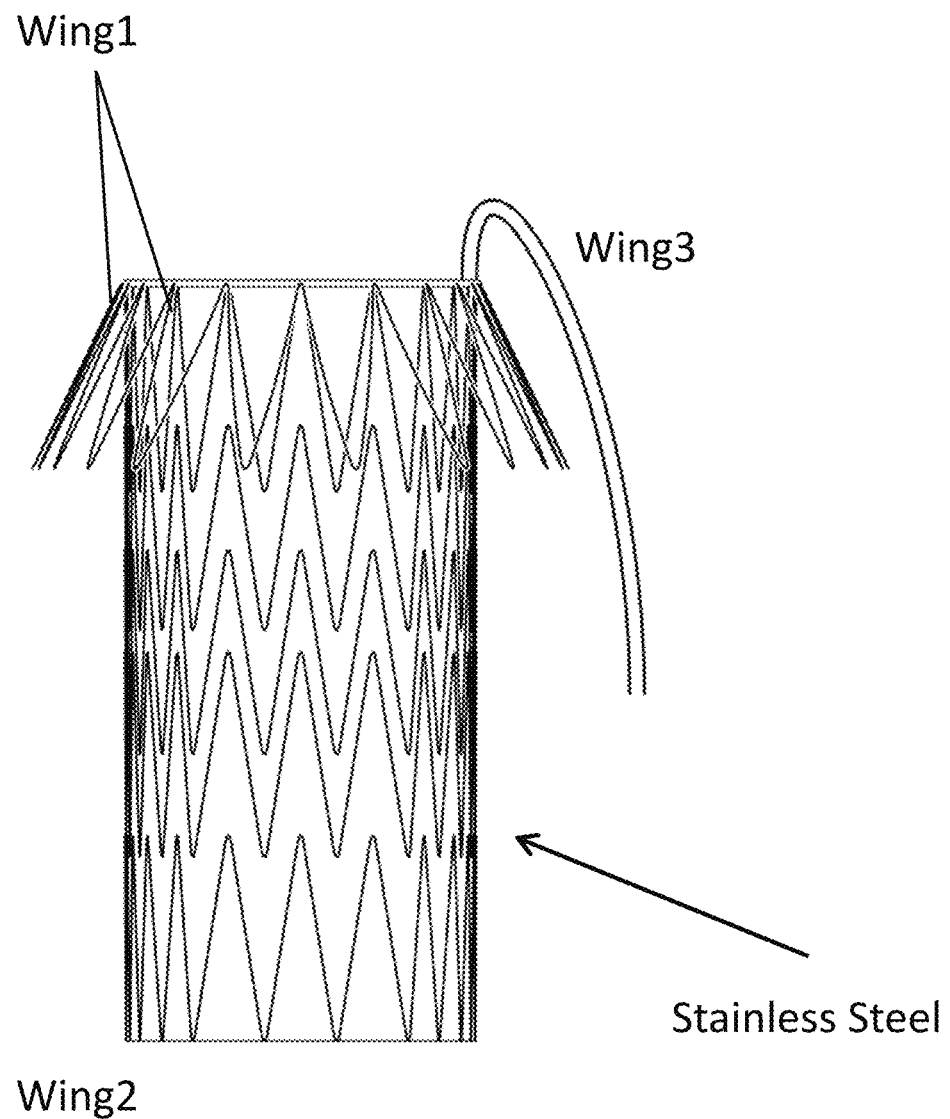
FIG. 12 is an image showing a prototype device having first, second and third wings projecting from predefined angles from a stainless steel structure.

With reference to FIGS. 8A-8G, an experimental setup and data is shown. FIGS. 8A-8C show images of an assembly including a prototype aorta root, graft with magnets and ascending aorta. FIG. 8D shows a preferred magnet thickness and FIG. 8E shows a graph of changes in spring constant. FIG. 8F shows images of an experimental setup for testing magnet configurations. FIG. 8G shows peak force at which the object starts to move and result data for two magnet configurations. FIG. 9A shows an experimental setup for a pulsatile flow test and FIGS. 9B shows a chart of results for different vacuum pressures and flow rates. FIG. 9C shows an experimental setup for an 8-magnet configuration at high conditions, and FIG. 9D shows related results data. FIG. 9E shows an experimental setup for a 4-magnet configuration at high conditions, and FIG. 9F shows related results data. FIG. 10 shows an experimental setup and related results data for a magnet test. FIG. 11A shows an experimental setup for measuring magnet attraction forces for different sized magnets. FIG. 11B shows magnetic attraction force measurement data for different sized magnets. FIG. 12 shows a prototype 600 device having first 602, second 604 and third 606 wings projecting from predefined angles from a stainless steel structure.

Embodiments of transcatheter devices for treating Type A dissection of Aorta described herein include several advantages, including a woven nitinol frame that is shaped as per the contours of the aortic root to establish the continuity and integrity of the aortic valve, a specially designed flexible, magnetic catheter that reconstitutes as a stent scaffold once delivered in the lumen of the aorta and can be customized to the size and shape of the aorta, using magnetism to reconstitute and hold together the separated layers of the aorta, and currently other than open heart surgery, there are no alternatives. The transcatheter approach doesn't involve open heart surgery, has minimal blood loss and minimal alterations to the patients physiology in a very sick patient, has the ability to reconstitute valve and maintain its integrity, features a small delivery profile allowing for smaller delivery sheaths and causing less vascular trauma, and the ability to customize and reposition. Economic benefits include better patient outcomes, a larger market than currently exists for open heart surgery, reduced operative trauma, reduced hospital stay, earlier recovery and an earlier return to work.

The disclosures of each and every patent, patent application, and publication cited herein are hereby incorporated herein by reference in their entirety. While this invention has been disclosed with reference to specific embodiments, it is apparent that other embodiments and variations of this invention may be devised by others skilled in the art without departing from the true spirit and scope of the invention.

What is claimed is:

1. A method for treating aortic dissection comprising:
   providing a system comprising:
     a sinotubular junction magnetic array configured into the shape of a ring having a first plurality of magnetic elements,
     a counter-magnetic array having a second plurality of magnetic elements, and
     an ascending aortic stent graft comprising a third plurality of magnetic elements;
   positioning the sinotubular junction magnetic array at a sinotubular junction;
   advancing counter magnetic constructs from the femoral vein and positioning them in the right atrium adjacent to the sinotubular junction;
   expanding the sinotubular junction magnetic array at a target position using magnetic forces;

advancing the counter magnetic array as one of the counter magnetic constructs used to form an at least partial circumferential seal; and advancing and positioning the ascending aortic stent graft within an interior of the sinotubular junction magnetic array.

2. The method of claim 1, wherein the poles of the first plurality of magnetic elements are configured to correspond with the poles of the second plurality of magnetic elements.

3. The method of claim 1, wherein the ascending aortic stent graft comprises a plurality of extension wings.

4. The method of claim 3, wherein the plurality of extension wings comprises three extension wings equally spaced apart.

5. The method of claim 1, wherein the sinotubular junction magnetic array comprises a lumen.

6. The method of claim 1, wherein the ascending aortic stent graft comprises a plurality of extension wings.

7. The method of claim 6, wherein the plurality of extension wings comprises three wings equally spaced apart.

* * * * *